US009023802B2

(12) United States Patent
Rammensee et al.

(10) Patent No.: US 9,023,802 B2
(45) Date of Patent: May 5, 2015

(54) HLA-BINDING PEPTIDES DERIVED FROM PROSTATE-ASSOCIATED ANTIGENIC MOLECULES AND METHODS OF USE THEREOF

(75) Inventors: Hans Georg Rammensee, Tuebingen (DE); Stefan Stevanovic, Tuebingen (DE); Cecile Gouttefangeas, Tuebingen (DE); Toni Weinschenk, Aichwald (DE); Peter Lewandrowski, Tuenbingen-Hirschau (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 241 days.

(21) Appl. No.: 12/967,606

(22) Filed: Dec. 14, 2010

(65) Prior Publication Data
US 2012/0082691 A1 Apr. 5, 2012

Related U.S. Application Data

(60) Provisional application No. 61/286,279, filed on Dec. 14, 2009.

(51) Int. Cl.
*A61K 38/00* (2006.01)
*C07K 14/47* (2006.01)
*A61K 39/00* (2006.01)

(52) U.S. Cl.
CPC ......... *C07K 14/4748* (2013.01); *A61K 39/0011* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 3,169,094 | A | 2/1965 | Wretlind |
| 6,406,705 | B1 | 6/2002 | Davis et al. |
| 6,881,405 | B2 * | 4/2005 | Leveugle et al. ......... 424/130.1 |
| 7,833,970 | B2 | 11/2010 | Dengjel |
| 8,067,529 | B2 | 11/2011 | Rammensee et al. |

FOREIGN PATENT DOCUMENTS

| | | |
|---|---|---|
| EP | 1 642 905 | 4/2006 |
| EP | 1 760 088 | 3/2007 |
| WO | 95/18145 | 7/1995 |
| WO | 03/040165 | * 5/2003 |
| WO | 2004/067023 | 8/2004 |

OTHER PUBLICATIONS

Rammensee et al, Immunogenetics vol. 41 p. 178 (1995).*
Engelhard, Current Opinion in Immunology vol. 6 p. 13 (1994).*
Guo, et al Nature vol. 360 p. 384 (1992).*
Shastri et al J. Immunol. vol. 1995 vol. 155 p. 4339.*
Condon et al.; "DNA-Based Immunization by In Vivo Transfection of Dendritic Cells"; Nature Medicine; vol. 2; No. 10; Oct. 1996; pp. 1122-1127.
Gong et al.; "Induction of Antitumor Activity by Immunization With Fusions of Dendritic and Carcinoma Cells"; Nature Medicine; vol. 3; No. 5; May 1997; pp. 558-561.
Zhai et al. "Antigen-Specific Tumor Vaccines: Development and Characterization of Recombinant Adenoviruses Encoding MART1 or GP100 for Cancer Therapy"; J. Immunol.; vol. 156; Jan. 15, 1996; pp. 700-710; The American Association of Immunologists.
Graham et al. "Intramuscular Immunisation With MUC1 CDNA Can Protect C57 Mice Challenged With MUC1-Expressing Syngeneic Mouse Tumour Cells"; Int. J. Cancer; vol. 65; 1996; pp. 664-670; Wiley-Liss, Inc.
Burchell et al.; "The MUC1 Gene as an Immunogen: Use of Naked DNA and Role of Dendritic Cells"; Breast Cancer. Advances in Biology and Therapeutics; 1996; pp. 309-313; F. Calvo, M. Crepin, H. Magdelenat. EDS John Libbey Eurotext.
Zhou et al.; "A Distinct Pattern of Cytokine Gene Expression by Human CD83+ Blood Dendritic Cells"; Blood; vol. 86; No. 9; Nov. 1, 1995; pp. 3295-3301; The American Society of Hematology.
Roth et al.; "Activation of Cloned Human CD4+ TH1 and TH2 Cells by Blood Dendritic Cells"; Scand. J. Immunol; 43; 1996; pp. 646-651; Blackwell Science LTD.
Scheel et al.; "Therapeutic Anti-Tumor Immunity Triggered by Injections of Immunostimulating Single-Stranded RNA"; Eur. J. Immunol.; 2006; vol. 36; No. 10; pp. 2807-2816; Wiley-VCH.
Gouttefangeas et al.: "Immunomonitoring of a multi-peptide vaccination trial for prostate carcinoma patients"; Presented at Progress in Vaccination Against Cancer PIVAC-10 Conference; Sep. 2010.
Mami-Chouaib et al.; "TCRAlpha /Beta and TCRGamma/Delta CD4/CD8~ HLA-DR Alloreactive CTL Clones Do Not Use FAS/FAS Ligand Pathway to Lyse Their Specific Target Cells; Human Immunology; Nov. 1996; 51(1): pp. 13-22; American Society for Histocompatibility and Immunogenetics; Elsevier.
Ji et al; "Comprehensive Analsis of the Gene Expression Profiles in Human Gastric Cancer Cell Lines"; Oncogene; Sep. 19, 2002; 21(42): pp. 6549-6556.
Southwood et al.; "Several Common HLA-DR Types Share Largely Overlapping Peptide Binding Repertoires"; The Journal of Immunology; 1998; vol. 160: pp. 3363-3373; The American Association of Immunologists.
Setterblad et al; "B Cell Lipid Rafts Regulate Both Peptide-Dependent and Peptide Independent APC-T Cell Interaction"; The Journal of Immunology; 2004; vol. 173: pp. 1876-1886.
Tang et al.; "Adenovirus Hexon T-Cell Epitope is Recognized by Most Adults and is Restricted by HLA DP4, The Most Common Class li Allele"; Gene Therapy; 2004; vol. 11; pp. 1408-1415; Nature Publishing Group.
Vigneron et al.; "Identification of a New Peptide Recognized by Autologous Cytolytic T Lymphocytes on a Human Melanoma"; Cancer Immunity; Jul. 19, 2002; vol. 2; p. 9.
Mickelson et al.; "Two Homozygous Typing Cells Defining a Subgroup of HLA-DW6"; Hum Immunol.; Dec. 1980; vol. 1; No. 4: pp. 363-368; Elsevier North Holland, Inc.

(Continued)

*Primary Examiner* — Sheela J Huff
(74) *Attorney, Agent, or Firm* — Miles & Stockbridge PC

(57) ABSTRACT

Methods and compositions for immunotherapeutic treatment of prostate cancer are disclosed. Patients are treated with compositions comprising HLA-binding peptides derived from prostate-associated antigenic molecules, either with or without immunological adjuvants.

20 Claims, 21 Drawing Sheets

(56) References Cited

OTHER PUBLICATIONS

Schubert et al.; Rapid Degradation of a Large Fraction of Newly Synthesized Proteins by Proteasomes; Nature; 2000; vol. 404; No. 6779; pp. 770-774; Macmillan Magazines Ltd.
Qin, Z., et al.; "CD4+ T-Cell—Mediated Tumor Rejection Involves Inhibition of Angiogenesis That is Dependent on IFN Gamma Receptor Expression by Non-Hematopoietic Cells"; Immunity.; Jun. 2000; vol. 12; pp. 677-686; Cell Press.
Kennedy et al.; "CD4+ T Lymphocytes Play a Critical Role in Antibody Production and Tumor Immunity Against Simian Virus 40 Large Tumor Antigen"; Cancer Res.; Mar. 2003; vol. 63; pp. 1040-1045; American Association for Cancer Research.
Van Der Bruggens et al.; "Peptide Database"; Cancer Immunity: A Journal of the Cancer Research Institute; Initial Publication Date 2001; Last Updated Jan. 10, 2012; http://www.cancerimmunity.org/peptidedatabase/tcellepitopes.htm.
Institute for Cel Biology Department of Immunology; BMI Heidelberg; A Database of MHC Ligands and Peptide Motifs (Ver. 1.0); Last Updated Aug. 2, 2009; http:/www.syfpeithi.de.
Dengjel et al.; "Unexpected Abundance of HLA Class II Presented Peptides in Primary Renal Cell Carcinomas"; Clin Cancer Res.; 2006; vol. 12; No. 14; pp. 4163-4170; American Association for Cancer Research.
Linehan WM, et al.; "The Genetic Basis of Cancer of the Kidney"; J Urol.; Dec. 2003; vol. 170; No. 6PT1; pp. 2163-2172.
McCartey, et al.; "Targeting P53 for Adoptive T-Cell Immunotherapy"; Cancer Research; 1998; vol. 15; No. 58; pp. 2601-2605.
Disis, et al.; "Immunity to the HER-2/NEU Oncogenic Protein"; Vaccine Against Induced Cancers; CIBA Found. Symp.; 1994; vol. 187: pp. 198-211; Wiley Chechester.
Banchereau et al; "Immune and Clinical Responses in Patients With Metastatic Melanoma to CD34+ Progenitor-Derivied Dendritic Cell Vaccine"; Cancer Research; vol. 61; Sep. 1, 2001; pp. 6451-6458; American Association for Cancer Research.
Singh-Jasuja et al.; "Correlation of T-Cell Response, Clinical Activity and Regulatory T-Cell Levels in Renal Cell Carcinoma Patients Treated With IMA901, A Novel Multi-Peptide Vaccine"; ASCO Meeting; 2007; Poster # 3017; American Society of Clinical Oncology.
Staehler, M., et al.; An Open Label Study to Evaluate the Safety and Immunogenicity of the Peptide Based Cancer Vaccine IMA901; ASCO Meeting; vol. 25; No. 18S; 2007; Poster # 5098; American Society of Clinical Oncology.
Van Der Bruggen, et al.; "A Gene Encoding an Antigen Recognized by Cytolytic T Lymphocytes on a Human Melanoma"; Science; Dec. 13, 1991; vol. 254; No. 5038; pp. 1643-1647.
Cox, et al.; "Identification of a Peptide Recognized by Five Melanoma-Specific Human Cytotoxic T Cell Lines"; Science; 1994; vol. 264; No. 5159; pp. 716-719.
Stevanovic; "Identification of Tumor-Associated T-Cell Epitopes for Vaccine Development"; Nat. Rev. Cancer; 2002; 2(7): pp. 514-520; Nature Publishing Group.
Celis, et al.; Induction of Anti-Tumor Cytotoxic T Lymphocytes in Normal Humans Using Primary Cultures and Synthetic Peptide Epitopes; Proc. Nat'l Acad. Sci. USA; 1994; vol. 91; No. 6; pp. 2105-2109; Immunology.
Vogt et al.; "Ligand Motifs of HLA-DRB5*0101 and DRB1*1501 Molecules Delineated From Self-Peptides 1s"; J Immunol.; 1994; vol. 153; No. 4; pp. 1665-1673; The American Association of Immunologists.
Malcherek et al.; "Analysis of Allele-Specific Contact Sites of Natural HLA-DR17 Ligands"; J Immunol.; 1994; vol. 153; vol. 3; pp. 1141-1149; The American Association of Immunologists.
Manici S., et al.; "Melanoma Cells Present a Mage-3 Epitope to CD4+ Cytotoxic T Cells in Association With Histocompatibility Leukocyte Antigen DR11"; J Exp Med.; 1999; vol. 189; No. 5; pp. 871-876; The Rockefeller University Press.
Hammer et al.; "Peptide Binding Specificity of HLA-DR4 Molecules: Correlation With Rheumatoid Arthritis Association"; J Exp Med.; May 1995; vol. 181; No. 5; pp. 1847-1855; The Rockefeller University Press.
Tompkins et al.; "A Europium Fluoroimmunoassay for Measuring Binding of Antigen to Class II MHC Glycoproteins"; J Immunol Methods.; 1993; vol. 163; No. 2; pp. 209-216; Elsevier Science Publishers B.V.
Boyton et al.; Glutamic Acid Decarboxylase T Lymphocyte Responses Associated With Susceptibility or Resistance to Type I Diabetes: Analysis in Disease Discordant Human Twins, Non-Obese Diabetic Mice and HLA-DQ Transgenic Mice; Int Immunol.; 1998; vol. 10; No. 12; pp. 1765-1776; Japanese Society for Immunology.
Strubin et al.; The Complete Sequence of the MRNA for the HLA-DR-Associated Invariant Chain Reveals a Polypeptide With an Unusual Transmembrane Polarity; EMBO J.; 1984; vol. 3; No. 4; pp. 869-872; IRL Press Limited.
Meziere, et al.; "In Vivo T Helper Cell Response to Retro-Inverso Peptidomimetics1"; J. Immunol.; 1997; vol. 159; pp. 3230-3237; The American Association of Immunologists.
Coligan, et al. (Eds.); Current Protocols in Protein Science; John Wiley & Sons NY; 1995-2000; Chap 15; John Wiley & Sons, Inc.
Lu, et al.; "Improved Synthesis of 4-Alkoxybenzyl Alcohol Resin"; J. Org. Chem.; 1981; vol. 46: pp. 3433-3436; American Chemical Society.
Brunsvig et al.; "Telomerase Peptide Vaccination: A Phase I/II Study in Patients With Non-Small Cell Lung Cancer"; Cancer Immunol Immunother.; 2006; vol. 55; No. 12; pp. 1553-1564; Springer-Verlag.
Longenecker, et al.; "Immune Responses of Mice and Human Breast Cancer Patients Following Immunization With Synthetic Sialyl-TN Conjugated to KLH Plus Detox Adjuvant"; Ann. NY Acad. Sci.; 1993; vol. 690; pp. 276-291.
Dupuis et al.; "Dendritic Cells Internalize Vaccine Adjuvant After Intramuscular Injection"; Cell Immunol.; 1998; vol. 186; No. 1; pp. 18-27; Article No. CI981283; Academic Press.
Allison; "The Mode of Action of Immunological Adjuvants"; Dev Biol Stand. Basel, Karger; 1998; vol. 92: pp. 3-11.
Gabrilovich et al.; "IL-12 and Mutant P53 Peptide-Pulsed Dendritic Cells for the Specific Immunotherapy of Cancer"; J Immunother; 1997; vol. 6; pp. 414-418; Lippincott-Raven Publishers.
Krieg, Arthur M.; "Therapeutic Potential of Toll-Like Receptor 9 Activation"; Nature Reviews, Drug Discovery; Jun. 2006; vol. 5; pp. 471-484; Coley Pharmaceutical Group, Inc.
Murphy, et al; "Phase I Clinical Trial: T-Cell Therapy for Prostate Cancer Using Autologous Dendritic Cells Pulsed With HLA-A0201-Specific Peptides From Prostate-Specific Membrane Antigen"; The Prostate; 1996; vol. 29; pp. 371-380; Wiley-Liss, Inc.
Tjoa, et al.; "Follow-Up Evaluation of Prostate Cancer Patients Infused With Autologous Dendritic Cells Pulsed With PSMA Peptides"; The Prostate; vol. 32; pp. 272-278; 1997; Wiley-Liss.
Gong, et al.; "Induction of Antigen-Specific Antitumor Immunity With Adenovirus-Transduced Dendritic Cells"; Gene Ther.; 1997; vol. 4; pp. 1023-1028; Stockton Press.
Wan, et al.; "Dendritic Cells Transduced With an Adenoviral Vector Encoding a Model Tumor-Associated Antigen for Tumor Vaccination"; Hum. Gene Ther.; Jul. 1997; vol. 8; pp. 1355-1363; Mary Ann Liebert, Inc.
Specht et al.; "Dendritic Cells Retrovirally Transduced With a Model Antigen Gene are Therapeutically Effective Against Established Pulmonary Metastases"; The Journal of Experimental Medicine; vol. 186; No. 8; Oct. 20, 1997; pp. 1213-1221.
Szabolcs et al.; "Retrovirally Transduced Human Dendritic Cells Express a Normal Phenotype and Potent T-Cell Stimulatory Capacity"; Blood; vol. 90; No. 6; Sep. 15, 1997; pp. 2160-2167.
Tueting et al.; "Genetically Modified Bone Marrow-Derived Dendritic Cells Expressing Tumor-Associated Viral or "Self" Antigens Induce Antitumor Immunity In Vivo"; Eur. J. Immunol.; 1997; vol. 27; pp. 2702-2707.
Ashley et al.; "Bone Marrow-Generated Dendritic Cells Pulsed With Tumor Extracts or Tumor RNA Induce Antitumor Immunity Against

(56) References Cited

OTHER PUBLICATIONS

Central Nervous System Tumors"; J. Exp. MD.; vol. 186; No. 7; Oct. 6, 1997; pp. 1177-1182; The Rockefeller University Press.

Strickley ; "Solubilizing Excipients in Oral and Injectable Formulations;" Pharmaceutical Research; vol. 21; No. 2; Feb. 2004; Plenum Publishing Corporation.

Thomas et al.; "Mesothelin-Specific CD8+ T Cell Responses Provide Evidence of In Vivo Cross-Priming by Antigen-Presenting Cells in Vaccinated Pancreatic Cancer Patients"; J. Exp. Med.; vol. 200, No. 3; Aug. 2004; pp. 297-306; The Rockefeller University Press.

Conroy et al.; "Polynucleotide-Mediated Immunization Therapy of Cancer"; Seminars in Oncology; vol. 23; No. 1; Feb. 1996; pp. 135-147; W. B. Saunders Company.

Murphy, et al., Janeway's immunobiology, 7th Ed., Chapter 5, pp. 181-214 (Garland Sci., Nov. 27, 2007).

Murphy, et al., Janeway's immunobiology, 7th Ed., Chapter 8, pp. 323-373 (Garland Sci., Nov. 27, 2007).

Walter, et al., Multipeptide immune response to cancer vaccine IMA901 after single-dose cyclophosphamide associates with longer patient survival, Nature Medicine vol. 18, No. 8, pp. 1254-1261 (Aug. 2012).

* cited by examiner

Figure 1

| Protein | Pos. | Sequence | SEQ ID NO |
|---|---|---|---|
| PSA | 141-150 | FLTPKKLQCV | 1 |
| | 146-154 | KLQCVDLHV | 2 |
| | 154-163 | VISNDVCAQV | 3 |
| PSCA | 14-22 | ALQPGTALL | 4 |
| | 105-113 | AILALLPAL | 5 |
| PSMA | 4-12 | LLHETDSAV | 6 |
| | 711-719 | ALFDIESKV | 7 |
| Survivin | 95-104 | ELTLGEFLKL | 8 |
| | 5-14 | TLPPAWQPFL | 9 |
| TRP-P8 | 187-195 | GLMKYIGEV | 10 |
| PROSTEIN | 31-39 | CLAAGITYV | 11 |
| Influenza MP | 58-66 | GILGFVFTL | 12 |
| PSMA | 459-473 | NYTLRVDCTPLMYSL | 13 |
| Survivin | 97-111 | TLGEFLKLDRERAKN | 14 |

Figure 2

|  | n | % | Geometric Mean | Range |
|---|---|---|---|---|
| PSA DT prior vaccination in months | 19 |  | 8.4 | 1.5–44.8 |
| PSA DT at study end or at end of follow-up | 18* |  | 11.2 | 2.2–148.0 |
| Increased PSA DT continuing at end of study | 4 | 21 |  |  |
| No change of PSA DT during vaccination but decline after | 1 | 5 |  |  |
| Interim PSA decline or DT increase followed by DT decrease | 3 | 16 |  |  |
| No change of PSA DT during vaccination | 11 | 58 |  | 2.2–44.8 |

\* PSA DT at study end or end of follow-up was not included for Pat. 5 owing to PSA decline

| Response of DT prior, during and after vaccination | | | |
|---|---|---|---|
| | DT prior vaccination [months] | DT during vaccination [months] | DT after vaccination [months] |
| *PSA stability and increase in DT* | | | |
| Pat 3 | 9.8 | -2.3 | 20.5 |
| Pat 8 | 6.6 | 148.0 | 148.0 |
| Pat 11 | 1.5 | 10.1 | |
| Pat 16 | 6.1 | -2.7 | 14.4 |
| geometric mean DT | 4.9 | | 25.8 |
| *Interim PSA rise followed by PSA decline and increase in PSA DT* | | | |
| Pat 5 | 3.2 | | -20.2 |
| *Interim PSA decline or stability followed by accelerated rise in PSA* | | | |
| Pat 7 | 3.7 | 21.5 | 2.8 |
| Pat 15 | 1.3 | 9.9 | 7.4 |
| Pat 17 | 10.2 | -1.9 | 4.8 |

A negative DT indicates the respective half time of PSA.

Table IV: PSA stability with no rise greater than 10% from baseline PSA

| | PSA baseline ng/ml | PSA end of study ng/ml | PSA end of follow up ng/ml | Months since baseline |
|---|---|---|---|---|
| Pat 3 | 0.58 | 0.51 | 0.73 | 31 |
| Pat 8 | 1.76 | 1.84 | 1.85 | 28 |

Figure 3

| No adjuvants | Response | Imiquimod | Response | Hyper-thermia | Response | GmCSF | Response | RNA | Response |
|---|---|---|---|---|---|---|---|---|---|
| Pat 1 | - | Pat 3 | + | Pat 13 | - | Pat 4 | - | Pat 16 | + |
| Pat 2 | - | Pat 7 | +/- | Pat 10 | - | Pat 6 | - | Pat 17 | +/- |
| Pat 5 | -/+ | Pat 8 | + | | | Pat 12 | - | Pat 18 | - |
| | | Pat 11 | + | | | Pat 14 | - | Pat 19 | - |
| | | | | | | Pat 15 | +/- | | |
| | | | | | | Pat 9 | - | | |

No response (-), interim PSA decline or stability followed by accelerated rise of PSA (+/-) or interim PSA rise followed by PSA decline and increase of PSA DT(-/+), increase of PSA DT (+).

Figure 4 after 10 weeks:
1 – 2.5 x 10⁷ cells /clone

| Clone # | name | PSMA | Surv |
|---|---|---|---|
| 1 | 15-1_A | - | - |
| 2 | 15-1_B | - | - |
| 3 | 15-10_A | 36% | 14% |
| 4 | 15-10_B | - | - |
| 5 | 15-10_D | - | - |
| 6 | 15-10_G | - | - |
| 7 | 15-10_M | - | 73% |
| 8 | 15-10_C | - | 0.90% |
| 9 | 15-10_F | - | 77% |
| 10 | 15-10_I | - | 76% |
| 11 | 15-10_Q | 36% | - |
| 12 | 15-10_O | - | 86% |
| 13 | 15-10_E | - | 59% |
| 14 | 15-10_V | 71% | 3% |
| 15 | 15-10_S | - | - |
| 16 | 15-10_H | - | 12% |
| 17 | 15-10_R | - | 61% |
| 18 | 15-10_T | 1% | 21% |
| 19 | 15-10_P | - | - |
| 20 | 26-10_A | - | - |
| 21 | 26-10_B | 44% | - |
| 22 | 26-10_C | - | 63% |
| 23 | 26-10_D | 3% | - |
| 24 | 26-10_X | - | - |
| 25 | 26-10_R | - | 89% |
| 26 | 26-10_F | 33% | - |
| 27 | 26-10_S | 5% | - |
| 28 | 26-10_E | 14% | 8% |
| 29 | 26-10_P | - | - |
| 30 | 26-10_H | - | - |
| 31 | 26-1_B | - | 2% |
| 32 | 26-1_C | 93% | - |
| 33 | 26-1_D | 87% | - |
| 34 | 26-1_F | 48% | - |

Figure 13

Survivin: HLA-DR binding prediction

DR1 (28/43), DR3 (29/40), DR4 (28/28), DR7 (16/34), DR11 (32/38), DR15 (30/34)

| | | Pro26<br>(DR1, DR13, DRB3, DQ5, DQ6) | Pro15<br>(DR1, DR11, DRB3, DQ3, DQ5) |
|---|---|---|---|
| AL | DR1, DQ1 | +++ | +++ |
| LAM | DQ3, DR4, DP4, DQA1*03 | - | - |
| HO301 | DQ5, DR6, DP19 | +++ | ++ |
| BM15 | DR11, DRB3, DQ3 | +++ | + |
| MGAR | DQ6, DR15, DP4, DW2 | - | - |
| LG2-EBV | DQ5, DRB3, DR14, DR7, DQB1*02 | n.t. | n.t. |
| EMJ | DR13, DQ1, DP3,4, DW19 | n.t. | n.t. |

TNFα responses: (-) < 0.1% CD4+, (+) > 3x control, (++) > 5x control, (+++) > 10x control

Figure 21

SEQUENCE LISTING

```
<160> NUMBER OF SEQ ID NOS: 42

<210> SEQ ID NO 1
<211> LENGTH: 10
<212> TYPE: PRT
<213> ORGANISM: Homo sapiens

<400> SEQUENCE: 1

Phe Leu Thr Pro Lys Lys Leu Gln Cys Val
1               5                   10

<210> SEQ ID NO 2
<211> LENGTH: 9
<212> TYPE: PRT
<213> ORGANISM: Homo sapiens

<400> SEQUENCE: 2

Lys Leu Gln Cys Val Asp Leu His Val
1               5

<210> SEQ ID NO 3
<211> LENGTH: 10
<212> TYPE: PRT
<213> ORGANISM: Homo sapiens
```

```
<400> SEQUENCE: 3

Val Ile Ser Asn Asp Val Cys Ala Gln Val
1               5                   10

<210> SEQ ID NO 4
<211> LENGTH: 9
<212> TYPE: PRT
<213> ORGANISM: Homo sapiens

<400> SEQUENCE: 4

Ala Leu Gln Pro Gly Thr Ala Leu Leu
1               5

<210> SEQ ID NO 5
<211> LENGTH: 9
<212> TYPE: PRT
<213> ORGANISM: Homo sapiens

<400> SEQUENCE: 5

Ala Ile Leu Ala Leu Leu Pro Ala Leu
1               5

<210> SEQ ID NO 6
<211> LENGTH: 9
<212> TYPE: PRT
<213> ORGANISM: Homo sapiens

<400> SEQUENCE: 6

Leu Leu His Glu Thr Asp Ser Ala Val
1               5

<210> SEQ ID NO 7
<211> LENGTH: 9
<212> TYPE: PRT
<213> ORGANISM: Homo sapiens

<400> SEQUENCE: 7

Ala Leu Phe Asp Ile Glu Ser Lys Val
1               5

<210> SEQ ID NO 8
<211> LENGTH: 10
<212> TYPE: PRT
<213> ORGANISM: Homo sapiens

<400> SEQUENCE: 8

Glu Leu Thr Leu Gly Glu Phe Leu Lys Leu
1               5                   10

<210> SEQ ID NO 9
<211> LENGTH: 10
<212> TYPE: PRT
<213> ORGANISM: Homo sapiens

<400> SEQUENCE: 9

Thr Leu Pro Pro Ala Trp Gln Pro Phe Leu
1               5                   10

<210> SEQ ID NO 10
<211> LENGTH: 9
<212> TYPE: PRT
<213> ORGANISM: Homo sapiens

<400> SEQUENCE: 10
```

```
Gly Leu Met Lys Tyr Ile Gly Glu Val
1               5

<210> SEQ ID NO 11
<211> LENGTH: 9
<212> TYPE: PRT
<213> ORGANISM: Homo sapiens

<400> SEQUENCE: 11

Cys Leu Ala Ala Gly Ile Thr Tyr Val
1               5

<210> SEQ ID NO 12
<211> LENGTH: 9
<212> TYPE: PRT
<213> ORGANISM: Homo sapiens

<400> SEQUENCE: 12

Gly Ile Leu Gly Phe Val Phe Thr Leu
1               5

<210> SEQ ID NO 13
<211> LENGTH: 15
<212> TYPE: PRT
<213> ORGANISM: Homo sapiens

<400> SEQUENCE: 13

Asn Tyr Thr Leu Arg Val Asp Cys Thr Pro Leu Met Tyr Ser Leu
1               5                   10                  15

<210> SEQ ID NO 14
<211> LENGTH: 15
<212> TYPE: PRT
<213> ORGANISM: Homo sapiens

<400> SEQUENCE: 14

Thr Leu Gly Glu Phe Leu Lys Leu Asp Arg Glu Arg Ala Lys Asn
1               5                   10                  15

<210> SEQ ID NO 15
<211> LENGTH: 14
<212> TYPE: PRT
<213> ORGANISM: Homo sapiens

<400> SEQUENCE: 15

Asp Phe Ile Ala Thr Leu Gly Lys Leu Ser Gly Leu His Gly
1               5                   10

<210> SEQ ID NO 16
<211> LENGTH: 9
<212> TYPE: PRT
<213> ORGANISM: Homo sapiens

<400> SEQUENCE: 16

Ala Thr Val Leu Phe Gly Ile Ala Arg
1               5

<210> SEQ ID NO 17
<211> LENGTH: 10
<212> TYPE: PRT
<213> ORGANISM: Homo sapiens

<400> SEQUENCE: 17

Ala Val Cys Gly Gly Val Leu Val His Pro
```

```
1               5                   10
```

<210> SEQ ID NO 18
<211> LENGTH: 11
<212> TYPE: PRT
<213> ORGANISM: Homo sapiens

<400> SEQUENCE: 18

```
Ala Val Cys Gly Gly Val Leu Val His Pro Gln
1               5                   10
```

<210> SEQ ID NO 19
<211> LENGTH: 9
<212> TYPE: PRT
<213> ORGANISM: Homo sapiens

<400> SEQUENCE: 19

```
Asp Gln Leu Asx Phe Leu Glu Arg Ala
1               5
```

<210> SEQ ID NO 20
<211> LENGTH: 9
<212> TYPE: PRT
<213> ORGANISM: Homo sapiens

<400> SEQUENCE: 20

```
Asp Tyr Asn Phe Val Phe Thr Ser Phe
1               5
```

<210> SEQ ID NO 21
<211> LENGTH: 11
<212> TYPE: PRT
<213> ORGANISM: Homo sapiens

<400> SEQUENCE: 21

```
Glu Val Ile Gly His Tyr Pro Gly Ser Ser Phe
1               5                   10
```

<210> SEQ ID NO 22
<211> LENGTH: 9
<212> TYPE: PRT
<213> ORGANISM: Homo sapiens

<400> SEQUENCE: 22

```
Glu Val Ile Thr Gly Ile Arg Ile Ile
1               5
```

<210> SEQ ID NO 23
<211> LENGTH: 9
<212> TYPE: PRT
<213> ORGANISM: Homo sapiens

<400> SEQUENCE: 23

```
Leu Leu Pro Pro Pro Pro Leu Leu Ala
1               5
```

<210> SEQ ID NO 24
<211> LENGTH: 9
<212> TYPE: PRT
<213> ORGANISM: Homo sapiens

<400> SEQUENCE: 24

```
Asn Ala Asp Pro Gln Ala Val Thr Met
1               5
```

```
<210> SEQ ID NO 25
<211> LENGTH: 9
<212> TYPE: PRT
<213> ORGANISM: Homo sapiens

<400> SEQUENCE: 25

Asn Tyr Glu Glu Thr Phe Pro His Ile
1               5

<210> SEQ ID NO 26
<211> LENGTH: 9
<212> TYPE: PRT
<213> ORGANISM: Homo sapiens

<400> SEQUENCE: 26

Ser Glu Ser Asp Thr Ile Arg Ser Ile
1               5

<210> SEQ ID NO 27
<211> LENGTH: 10
<212> TYPE: PRT
<213> ORGANISM: Homo sapiens

<400> SEQUENCE: 27

Ser Val Val Gly Gly Phe Val Ser His Tyr
1               5                   10

<210> SEQ ID NO 28
<211> LENGTH: 9
<212> TYPE: PRT
<213> ORGANISM: Homo sapiens

<400> SEQUENCE: 28

Ser Tyr Pro Tyr Tyr Pro Tyr Leu Tyr
1               5

<210> SEQ ID NO 29
<211> LENGTH: 11
<212> TYPE: PRT
<213> ORGANISM: Homo sapiens

<400> SEQUENCE: 29

Thr Ile Ile Asp Ser Asp Lys Ile Met Val Leu
1               5                   10

<210> SEQ ID NO 30
<211> LENGTH: 9
<212> TYPE: PRT
<213> ORGANISM: Homo sapiens

<400> SEQUENCE: 30

Thr Tyr Asp Phe Ala His Cys Thr Phe
1               5

<210> SEQ ID NO 31
<211> LENGTH: 10
<212> TYPE: PRT
<213> ORGANISM: Homo sapiens

<400> SEQUENCE: 31

Val Phe Asp Thr Ala Ile Ala His Leu Phe
1               5                   10

<210> SEQ ID NO 32
```

```
<211> LENGTH: 9
<212> TYPE: PRT
<213> ORGANISM: Homo sapiens

<400> SEQUENCE: 32

Val Tyr Asn Pro Thr Pro Asn Ser Leu
1               5

<210> SEQ ID NO 33
<211> LENGTH: 10
<212> TYPE: PRT
<213> ORGANISM: Homo sapiens

<400> SEQUENCE: 33

Tyr Thr Ile Gly Leu Gly Leu His Ser Leu
1               5                   10

<210> SEQ ID NO 34
<211> LENGTH: 9
<212> TYPE: PRT
<213> ORGANISM: Homo sapiens

<400> SEQUENCE: 34

Ala Pro Leu Leu Leu Ala Arg Ala Ala
1               5

<210> SEQ ID NO 35
<211> LENGTH: 9
<212> TYPE: PRT
<213> ORGANISM: Homo sapiens

<400> SEQUENCE: 35

Lys Arg Ala Thr Gln Ile Pro Ser Tyr
1               5

<210> SEQ ID NO 36
<211> LENGTH: 8
<212> TYPE: PRT
<213> ORGANISM: Homo sapiens

<400> SEQUENCE: 36

Met Arg Ala Ala Pro Leu Leu Leu
1               5

<210> SEQ ID NO 37
<211> LENGTH: 9
<212> TYPE: PRT
<213> ORGANISM: Homo sapiens

<400> SEQUENCE: 37

Met Arg Ala Ala Pro Leu Leu Leu Ala
1               5

<210> SEQ ID NO 38
<211> LENGTH: 9
<212> TYPE: PRT
<213> ORGANISM: Homo sapiens

<400> SEQUENCE: 38

Phe Thr Glu Leu Thr Leu Gly Glu Phe
1               5

<210> SEQ ID NO 39
<211> LENGTH: 9
<212> TYPE: PRT
```

```
<213> ORGANISM: Homo sapiens

<400> SEQUENCE: 39

Leu Met Leu Gly Glu Phe Leu Lys Leu
1               5

<210> SEQ ID NO 40
<211> LENGTH: 9
<212> TYPE: PRT
<213> ORGANISM: Homo sapiens

<400> SEQUENCE: 40

Glu Pro Asp Leu Ala Gln Cys Phe Tyr
1               5

<210> SEQ ID NO 41
<211> LENGTH: 15
<212> TYPE: PRT
<213> ORGANISM: Homo sapiens

<400> SEQUENCE: 41

Thr Leu Gly Glu Phe Leu Lys Leu Asp Arg Glu Arg Ala Lys Asp
1               5                   10                  15

<210> SEQ ID NO 42
<211> LENGTH: 17
<212> TYPE: PRT
<213> ORGANISM: Homo sapiens

<400> SEQUENCE: 42

Glu Leu Thr Leu Gly Glu Phe Leu Lys Leu Asp Arg Glu Arg Ala Lys
1               5                   10                  15

Asn
```

HLA-BINDING PEPTIDES DERIVED FROM PROSTATE-ASSOCIATED ANTIGENIC MOLECULES AND METHODS OF USE THEREOF

CROSS REFERENCE TO RELATED APPLICATIONS

This application claims priority from U.S. Application 61/286,279, filed Dec. 14, 2009, the contents of which is incorporated herein by reference in its entirety.

FIELD OF THE INVENTION

Methods and compositions for immunotherapeutic treatment of prostate cancer are disclosed. More specifically methods of treating patients with prostate cancer comprising administering compositions comprising HLA-binding peptides derived from prostate-associated antigenic molecules, either with or without immunological adjuvants, are disclosed.

BACKGROUND

Prostate cancer is one of the most common malignancies in men with a reported incidence of 346,000 patients and approximately 87,000 deaths in Europe in 2006. It is the most common cancer diagnosis and the second leading cause of cancer related deaths in men in the United States. Because of the increasing sensitivity of prostate specific antigen (PSA) monitoring assays, prostate cancer is detected at an earlier and clinically localized stage, in which curative treatments like surgery and radiation can be performed. Nevertheless, these patients have a 10-60% chance of experiencing an asymptomatic increase of PSA within 10 years, known as a "biochemical relapse." Biochemical relapse often indicates a hidden local recurrence of the cancer or the onset of still undetectable metastases.

Therapeutic options in this situation include external radiotherapy and androgen deprivation (also known as hormone ablation). However, neither therapeutic approach has been proven effective, especially with respect to prolonging the patient's long-term survival. Moreover, both treatments are hampered by a number of side effects, including the increased risk of cardiovascular difficulties, osteoporosis, weight gain, neurocognitive decline, development of urethral strictures, loss of libido and impotence, the risk of a reduction in skeletal calcium salts in terms of osteoporosis, and a markedly increased risk of pathologic bone fractures. In addition, there is some concern that androgen deprivation permits early development of androgen-independent neoplastic clones, ultimately resulting in further and faster long-term tumor progression. Moreover, the optimal timing for initiation of androgen deprivation therapy is debated, particularly for biochemical relapses characterized by low PSA values or long mean doubling times (DT's). Given these risks, both androgen deprivation therapy and external radiotherapy are of questionable therapeutic value for patients experiencing an early biochemical relapse.

Tumor associated antigens ("TAAs") have been identified as potential cancer immunotherapeutic agents. Numerous TAAs specific for a variety of different tumor and tissue types have been identified, including those associated with the prostate. The identification of T-cells specific for TAAs in prostate tumor tissue, tumor-draining lymph nodes, and the peripheral circulatory system of cancer patients, as well as the increase of specific T-cell responses after immunotherapy, all suggest that manipulation of the immune system using TAAs could be useful in treating prostate cancer.

Various systems for in vivo antigenic presentation of prostate-specific TAAs have been tested in clinical trials, including: (1) vaccine therapy with autologous or allogeneic tumor cells; (2) autologous tumor cells engineered to express granulocyte-macrophage colony-stimulating factor; (3) dendritic cells pulsed ex vivo with HLA I and II-binding peptides; (4) tumor-mRNA transfected dendritic cells; and (5) recombinant vaccinia viruses expressing TAAs. However, most of these studies have been conducted in patients with androgen resistant prostate carcinoma. Little information is available about vaccination therapy in androgen-sensitive patients with a biochemical relapse prior to androgen deprivation therapy.

Therefore, new treatment options are needed for patients with prostate cancer, particularly patients with early biochemical relapse.

SUMMARY

The present disclosure relates to compositions for immunotherapeutic use and methods of use thereof. In particular, the present disclosure relates to the immunotherapy of cancer and more particularly, prostate cancer, and even more particularly, androgen-sensitive prostate cancer in patients with early biochemical relapse who have not received androgen deprivation therapy. The present disclosure further relates to compositions of HLA-binding peptides of both HLA class I and class II, said HLA-binding peptides being derived from prostate-associated antigenic molecules, such as prostate specific antigen, prostate stem cell antigen, prostate specific membrane antigen, survivin, prostein, and transient receptor potential-p8 ("TRP-p8").

In one aspect, the present disclosure relates to compositions comprising at least one HLA-binding peptide, wherein said HLA-binding peptide comprises an epitope derived from a prostate-associated antigenic molecule.

In another aspect, the present disclosure relates to compositions comprising at least one HLA-binding peptide, wherein said HLA-binding peptide comprises an epitope derived from a prostate-associated antigenic molecule selected from the group consisting of: prostate specific antigen; prostate stem cell antigen; prostate specific membrane antigen; survivin; prostein; and transient receptor potential-p8.

In a further aspect, the compositions of the present disclosure comprise an epitope according to SEQ ID NO: 24, SEQ ID NO: 7, SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 13, SEQ ID NO: 14, or SEQ ID NO: 15 to SEQ ID NO: 23, or SEQ ID NO: 25 to SEQ ID NO: 40.

In a further aspect, the compositions comprise at least two HLA-binding peptides comprising an epitope derived from a prostate-associated antigenic molecule, wherein at least one of the at least two HLA-binding peptides is an HLA class I peptide; and at least one of the at least two HLA-binding peptides is an HLA class II peptide.

Yet another aspect of the disclosure relates to compositions comprising at least two HLA-binding peptides, wherein at least one of the HLA-binding peptides is an HLA class I peptide comprising an epitope selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11; and at least one of the HLA-binding peptides is an HLA class II peptide comprising an epitope selected from the group consisting of: SEQ ID NO: 13 and SEQ ID NO: 14.

Yet another aspect of the disclosure relates to compositions comprising at least two HLA-binding peptides, wherein (a) at least one of the at least two HLA-binding peptides is a peptide comprising an epitope selected from the group consisting of: SEQ ID NO: 24, SEQ ID NO: 15 to SEQ ID NO: 23, and SEQ ID NO: 25 to SEQ ID NO: 37, and (b) at least one of the at least two peptides is a peptide comprising an epitope selected from the group consisting of: SEQ ID NO: 7, SEQ ID NO:1 to SEQ ID NO: 6, SEQ ID NO: 8 to SEQ ID NO: 11, SEQ ID NO: 13, SEQ ID NO: 14, and SEQ ID NO: 38 to SEQ ID NO: 42.

Yet another aspect of the disclosure relates to compositions comprising at least two HLA-binding peptides, wherein at least one of the HLA-binding peptides is an HLA class I peptide consisting essentially of an epitope selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11; and at least one of the HLA-binding peptides is an HLA class II peptide consisting essentially of an epitope selected from the group consisting of: SEQ ID NO: 13 and SEQ ID NO: 14.

Yet another aspect of the disclosure relates to compositions comprising at least two HLA-binding peptides, wherein at least one of the HLA-binding peptides is an HLA class I peptide consisting of an epitope selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11; and at least one of the HLA-binding peptides is an HLA class II peptide consisting of an epitope selected from the group consisting of: SEQ ID NO: 13 and SEQ ID NO: 14.

Yet another aspect of the disclosure relates to compositions comprising at least two HLA-binding peptides, wherein at least one of the HLA-binding peptides is an HLA class I peptide binding to an allele other than HLA-A*02.

Yet another aspect of the disclosure relates to compositions comprising at least two HLA-binding peptides, wherein at least one of the HLA-binding peptides is an HLA class I peptide binding to an allele selected from the group of HLA-A*24, HLA-A*11, HLA-B*41, HLA-B*51 or HLA-C.

Yet another aspect of the disclosure relates to compositions comprising at least six HLA-binding peptides, wherein: (a) at least one HLA-binding peptide comprises an epitope derived from prostate specific antigen; (b) at least one HLA-binding peptide comprises an epitope derived from prostate stem cell antigen; (c) at least one HLA-binding peptide comprises an epitope derived from prostate specific membrane antigen; (d) at least one HLA-binding peptide comprises an epitope derived from survivin; (e) at least one HLA-binding peptide comprises an epitope derived from prostein; and (f) at least one HLA-binding peptide comprises an epitope derived from transient receptor potential-p8.

Another aspect of the disclosure relates to compositions as described above wherein said composition comprises at least two peptides consisting of amino acid sequences according to group b).

Another aspect of the disclosure relates to compositions as described above comprising HLA-binding peptides according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42.

Another aspect of the disclosure relates to a composition as described above, wherein said composition comprises the peptides consisting of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, and SEQ ID NO: 14, and optionally at least one peptide selected from the group consisting of SEQ ID NO: 15 to SEQ ID NO: 42.

Another aspect of the disclosure relates to a composition as described above, wherein said composition comprises at least two peptides, preferably at least four peptides and more preferably ten peptides, consisting of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one peptide selected from the group consisting of SEQ ID NO: 15 to SEQ ID NO: 42.

Another aspect of the disclosure relates to a composition as described above, wherein said composition comprises at least two peptides, preferably at least four peptides and more preferably ten peptides, consisting of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one peptide selected from the group consisting of SEQ ID NO: 15 to SEQ ID NO: 42, wherein the additional peptide is selected according to the HLA set of the subject to be treated.

Another aspect of the disclosure then relates to a composition as described above, wherein said composition comprises at least four peptides consisting of the amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, and SEQ ID NO: 15 to SEQ ID NO: 42.

A further aspect of the disclosure relates to any of the previously described compositions, wherein at least one of the peptides is a class II peptide.

A further aspect of the disclosure relates to any of the previously described compositions further comprising an immunological adjuvant or a mixture of two or three immunological adjuvants, such as, for example, GMCSF and Imiquimod. The immunological adjuvant can be any known immunological adjuvant, including Toll-like receptor-7 agonists imiquimod and mucin-1-mRNA/protamine complex and the cytokine granulocyte macrophage colony stimulating factor ("GM-CSF").

An additional aspect of the disclosure then relates to methods of treating prostate cancer comprising administering to a patient any of the compositions disclosed herein, either with or without an immunological adjuvant. Said prostate cancer can be androgen sensitive, and the patient may have not received androgen deprivation therapy.

Another aspect of the disclosure then relates to a method of treating either androgen-sensitive or androgen-insensitive prostate cancer in a patient, said method comprising administering to the patient any of the previously described compositions, either with or without an immunological adjuvant.

BRIEF DESCRIPTION OF THE FIGURES

FIG. 1 shows the various epitopes comprised by the HLA-binding peptides in the HLA-binding peptide cocktail used in Example 1, including thirteen epitopes derived from prostate-associated antigenic molecules. The epitopes according to SEQ ID NO: 1 through SEQ ID NO: 12 are HLA class I epitopes, namely, HLA-A*201-restricted epitopes. The epitopes according to SEQ ID NO: 13 and SEQ ID NO: 14 are HLA class II epitopes.

FIG. 2 provides DT statistics for the study group as a whole. DT is indicated in months. "n" indicates the number of patients whose statistics were included in each category. "%" indicates the percentage of patients falling into each category. Patient 5's doubling time was not included in the calculation of the geometric mean or the range at the end of the study, owing to his the negative doubling time.

FIG. 3 shows the changes in DT prior to, during, and after treatment of patients with the HLA-binding cocktail used in Example 1. A positive figure indicates a PSA doubling time, which means that the patient's PSA levels are increasing. A negative figure indicates a PSA half-life, which means that the patient's PSA levels are decreasing.

FIG. 4 shows the clinical response to treatment as segregated by immunological adjuvant type. No clinical response is indicated by the "−" symbol. Interim PSA decline or stability followed by accelerated rise of PSA is indicated by the "+/−" symbol. Interim PSA rise followed by PSA decline and increase of PSA DT is indicated by the "−/+" symbol. Increase of PSA DT is indicated by the "+" symbol.

FIG. 13 shows the specificities of CD4+ T cells derived from the PBMCs of patient number 15 and patient number 26 for the PSMA 459-473 epitope and the survivin 97-111 epitope. PSMA: the PSMA 459-473 epitope. Surv: the survivin 97-111 epitope.

FIG. 21 shows that several tumor cell lines expressing different HLA-DR alleles are recognized by patient-derived PBMCs (shown for the patients Pro26 and Pro15). Patients develop multi-clonal T-cell responses after vaccination with survivin 97-111. Survivin 97-111 shows promiscuous binding to several HLA class II alleles: DR1; (see also Wang et al.); DQ5 (not tested by Wang et al.); DR11 (see also Wang et al.); or DRB3 (in contrast to Wang et al., 2008, Table 1). Functional presentation of survivin 97-111 is possible in the context of several HLA class II molecules (TNF-alpha production). As for HLA class I (HLA-A, -B, C), in principle, also three different gene loci can be found for HLA class II that express functional class II molecules on the cell surface, namely HLA-DQ, HLA-DP and HLA-DR. Class I molecules are composed of a heavy chain (-A, -B, -C) and a beta-2-microglobulin that is constant in all three genes. Nevertheless, class II molecules are composed of two each of variable chains (alpha and beta). Thus, sophisticated genetically typing is always complicated with class II. In the figure, so-called serologic types are given, which are based on antibody binding. Thus, "DQ3" for example comprises different alleles of HLA-DQ alpha and beta chains that are commonly found together and react with a particular antibody. The cells in the figure are as follows: AL=E418 EBV transformed B-cell line (Human Immunology Volume 51, Issue 1, November 1996, Pages 13-22); LAM=B lymphoma cell line (Oncogenomics 19 Sep. 2002, Volume 21, Number 42, Pages 6549-6556); HO301=EBV transformed B cell line (The Journal of Immunology, 1998, 160: 3363-3373); BM15=Dr11+APC cell line (The Journal of Immunology, 2004, 173: 1876-1886); MGAR=homozygous B-LCL (Gene Therapy (2004) 11, 1408-1415); LG2-EBV=autologous B cell line (Cancer Immunity, Vol. 2, p. 9 (19 Jul. 2002)); EMJ=B Lymphoblastoid Cell Line (ECACC NO: 8602103 IHW Number 9097: and Hum Immunol. 1980 December; 1(4):363-8).

DETAILED DESCRIPTION

Figure 5:
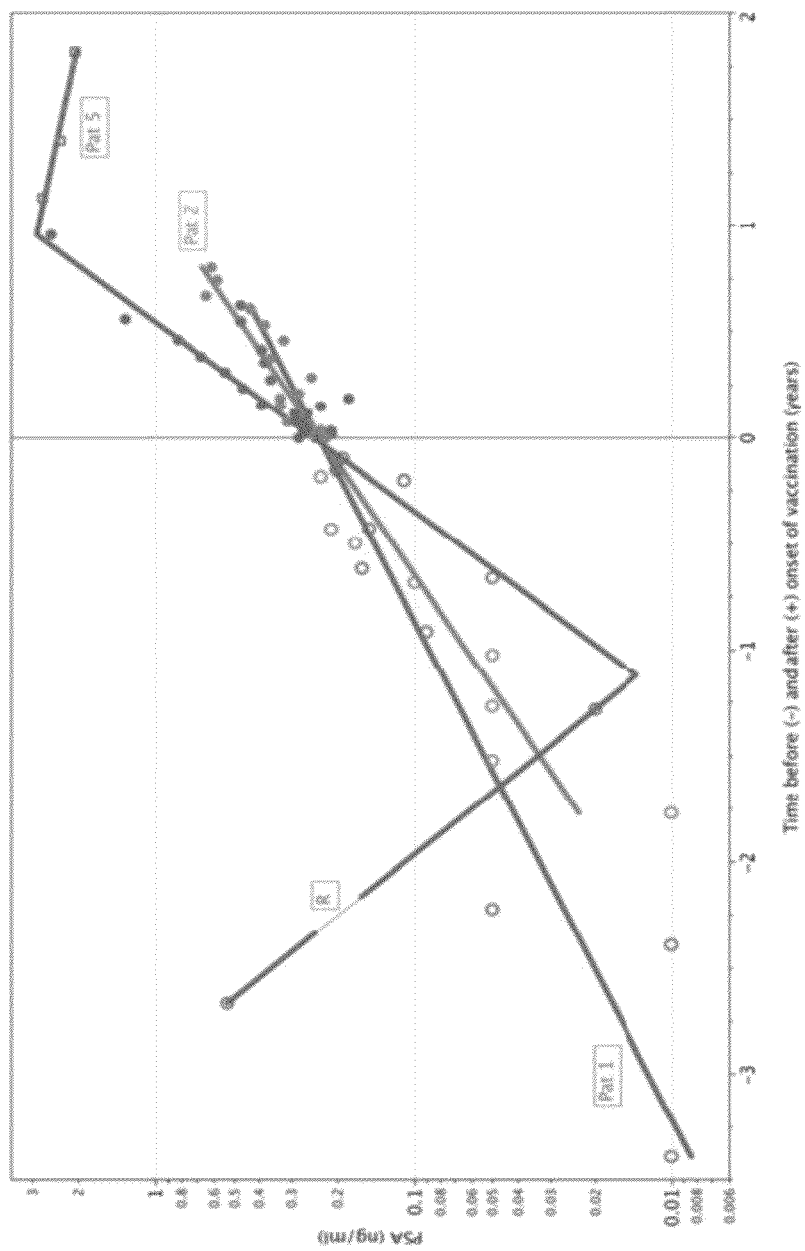
FIG. 5 shows PSA levels in patients receiving peptides in montanide, but no adjuvant or hyperthermia.
Figure 6:
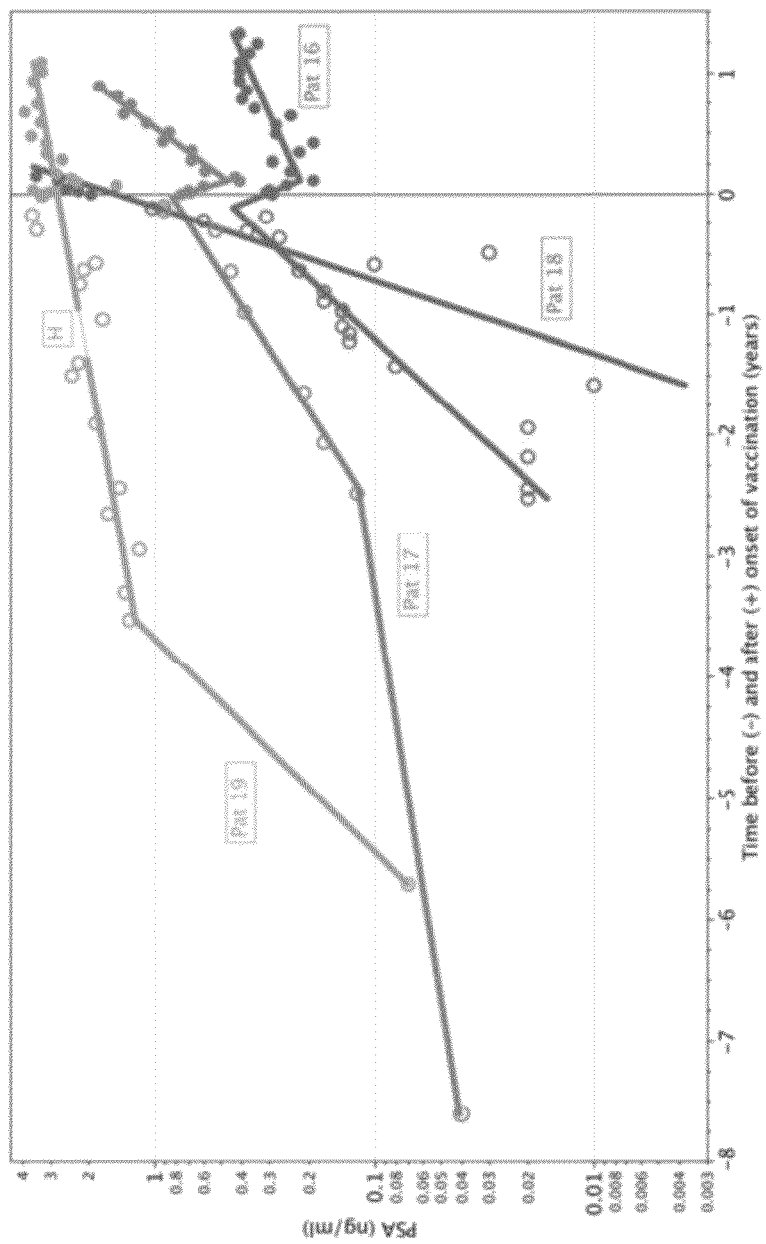
FIG. 6 shows PSA levels in patients receiving peptides in montanide, with mucin-1-mRNA/protamine complex.
Figure 7:
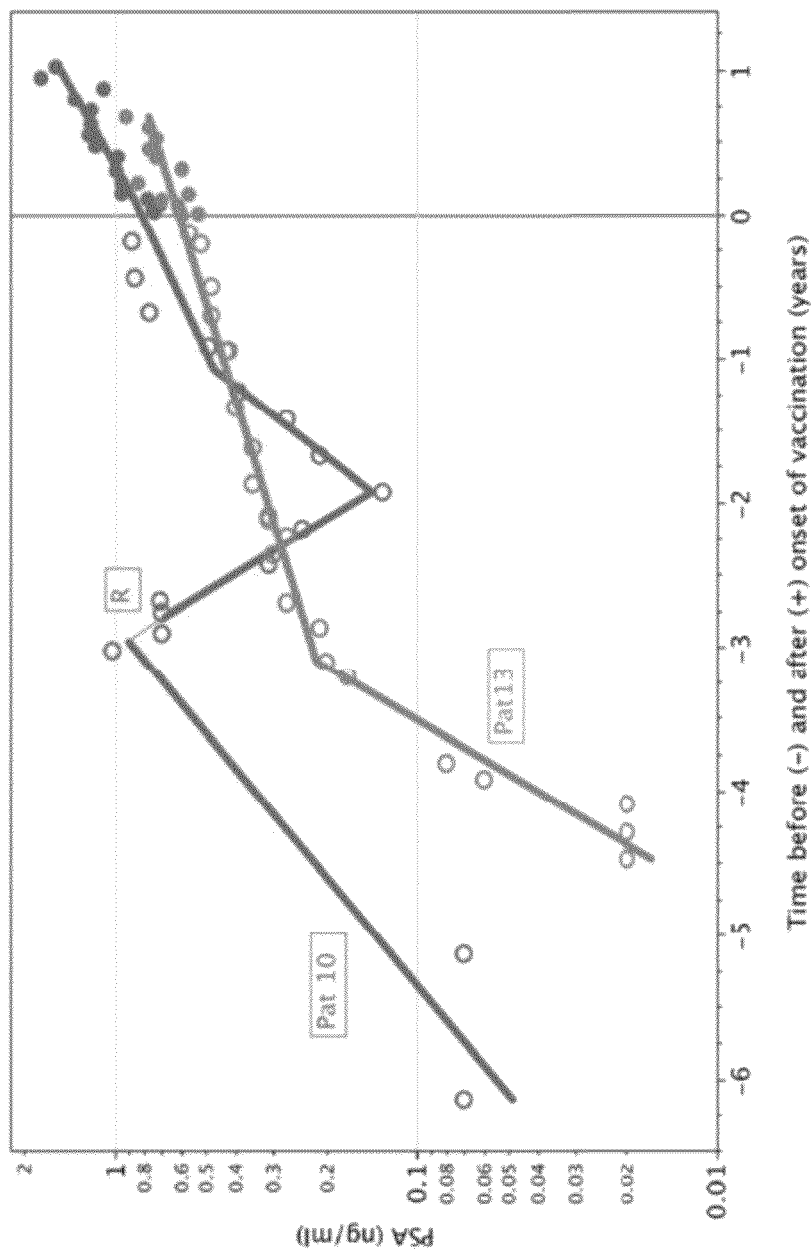
FIG. 7 shows PSA levels in patients receiving peptides in montanide, with hyperthermia.
Figure 8:
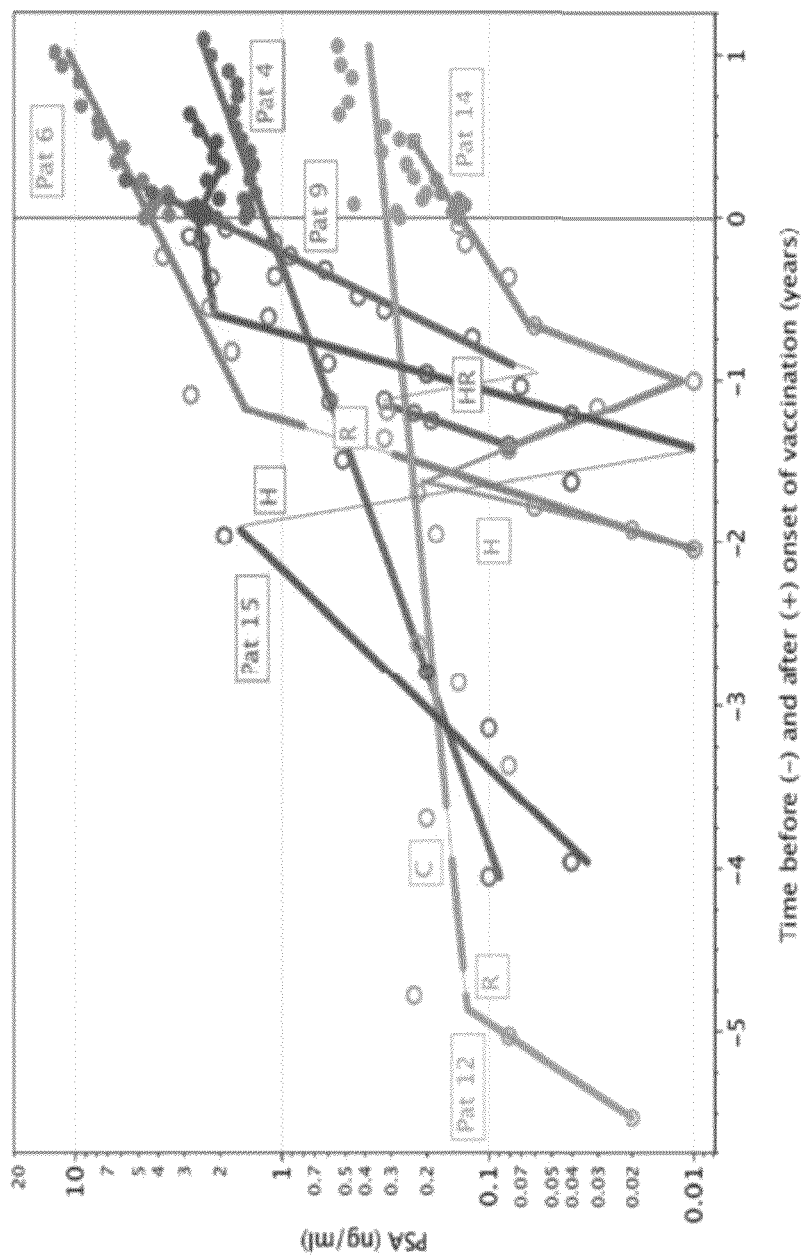
FIG. 8 shows PSA levels in patients receiving peptides in montanide, with GM-CSF.
Figure 9:
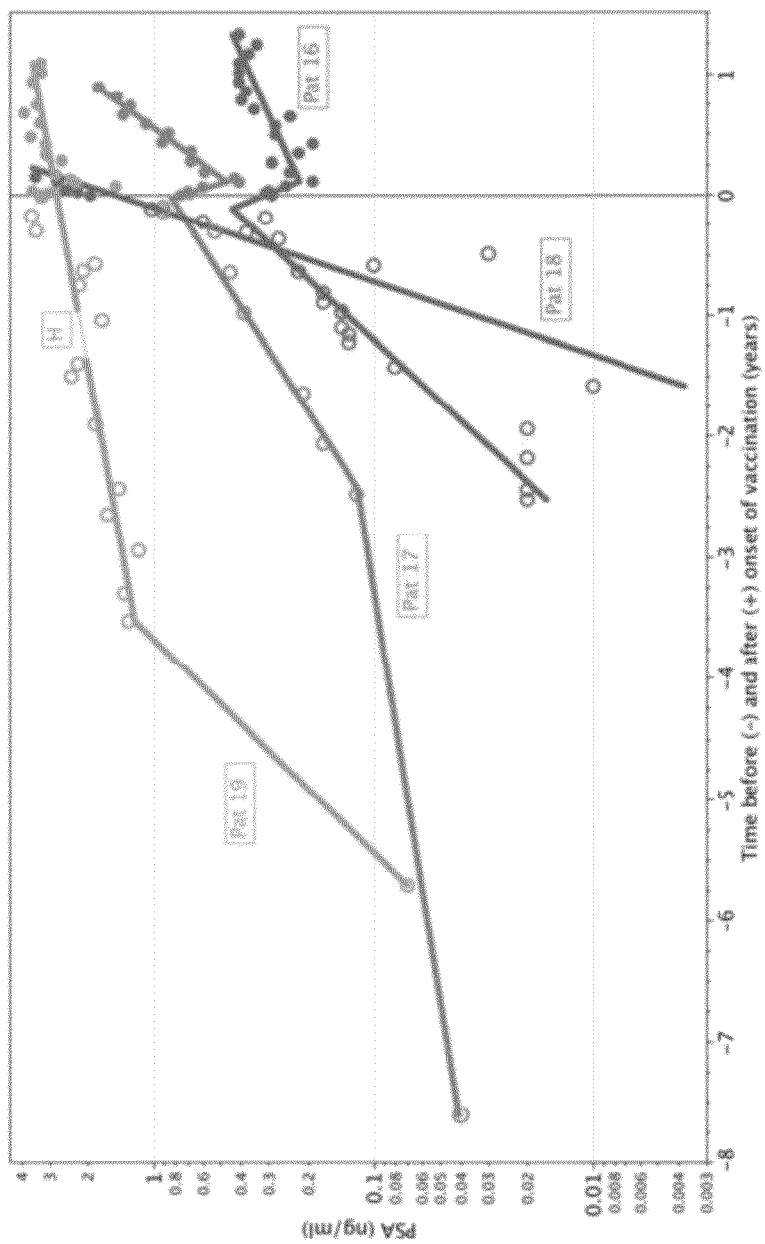
FIG. 9 shows PSA levels in patients receiving peptides in montanide, with imiquimod.
Figure 10:
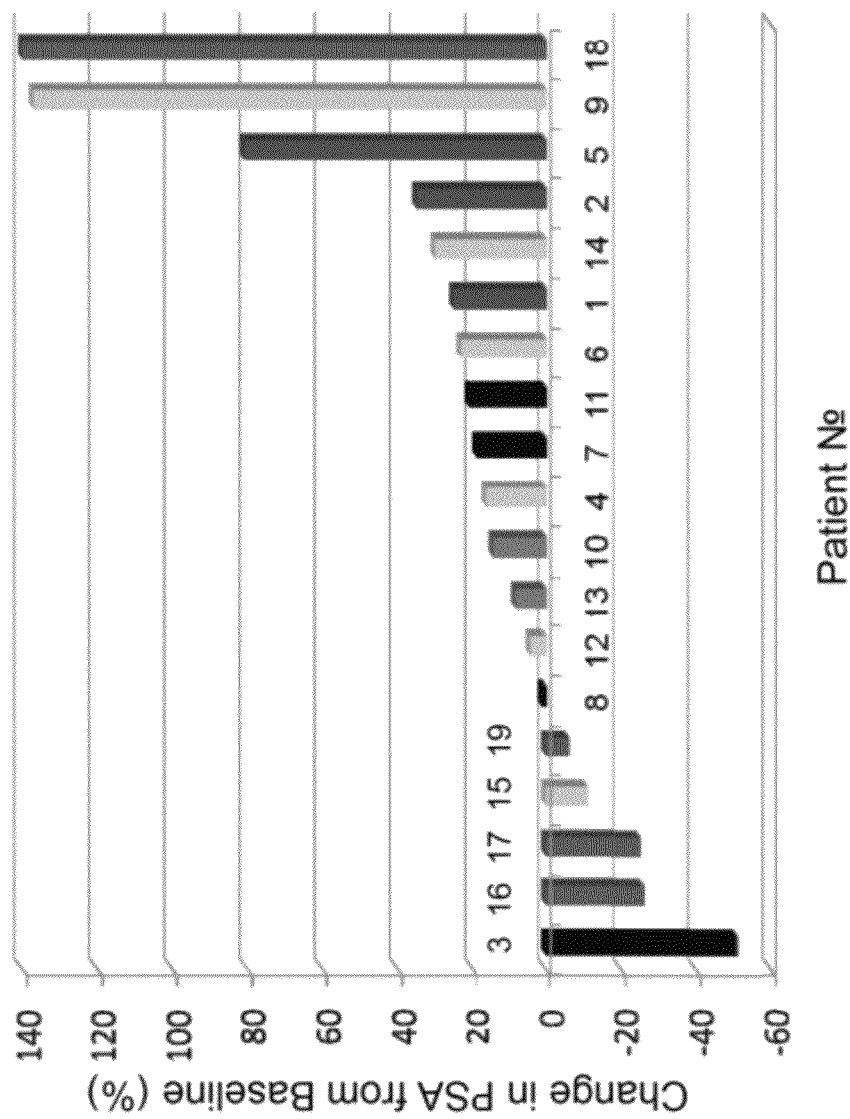
FIG. 10 shows changes in PSA value from baseline in percent at Day 84.
Figure 11:
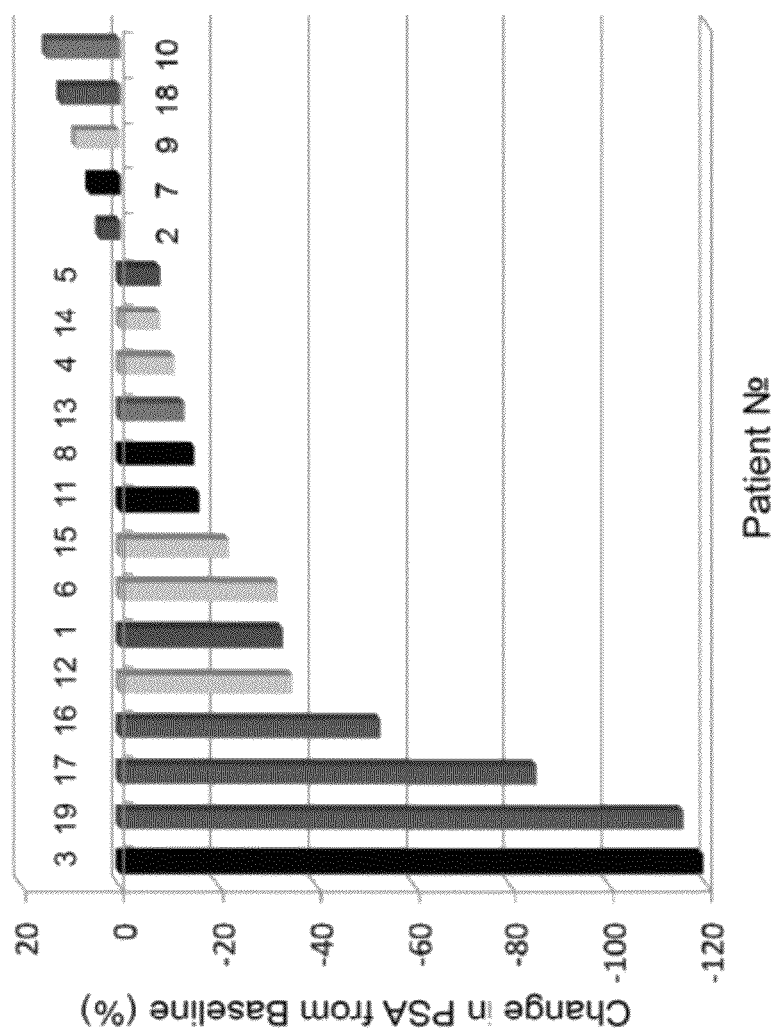
FIG. 11 shows change in PSA value in percent during vaccination.
Figure 12:
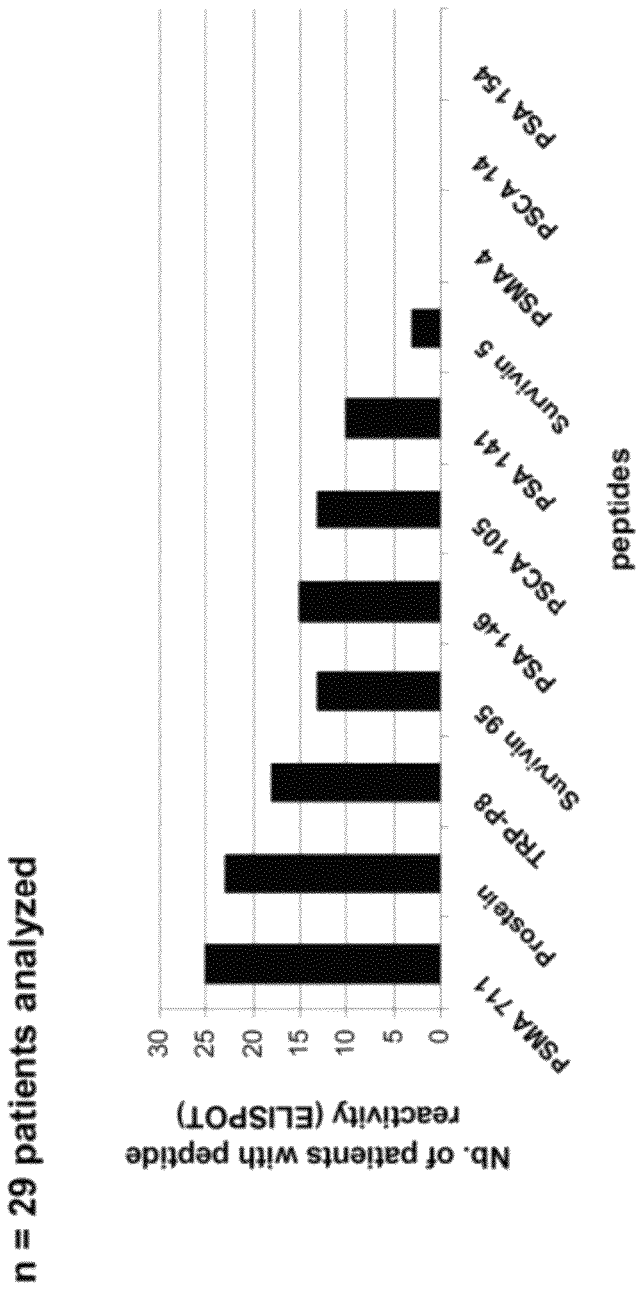
FIG. 12 shows the number of patients having T-cells that are reactive to each peptide after vaccination.
Figure 14:
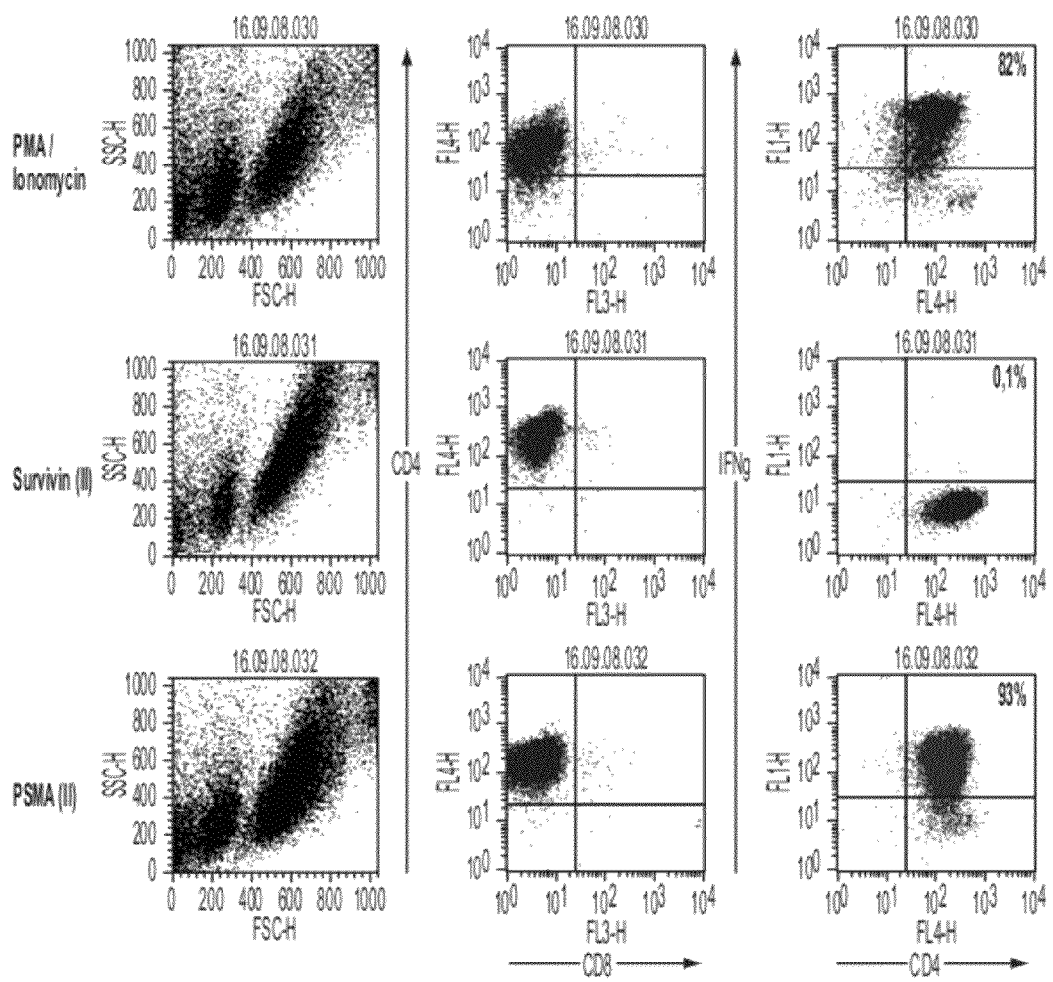
FIG. 14 shows peptide reactivity of clone Pro26_1 C. PMA/ionomycin=antigen-independent unspecific activation; Survivin (II): stimulation with the survivin 97-111 epitope; PSMA (II): stimulation with the PSMA 459-473 epitope. All reactive cells are CD4 positive.
Figure 15:
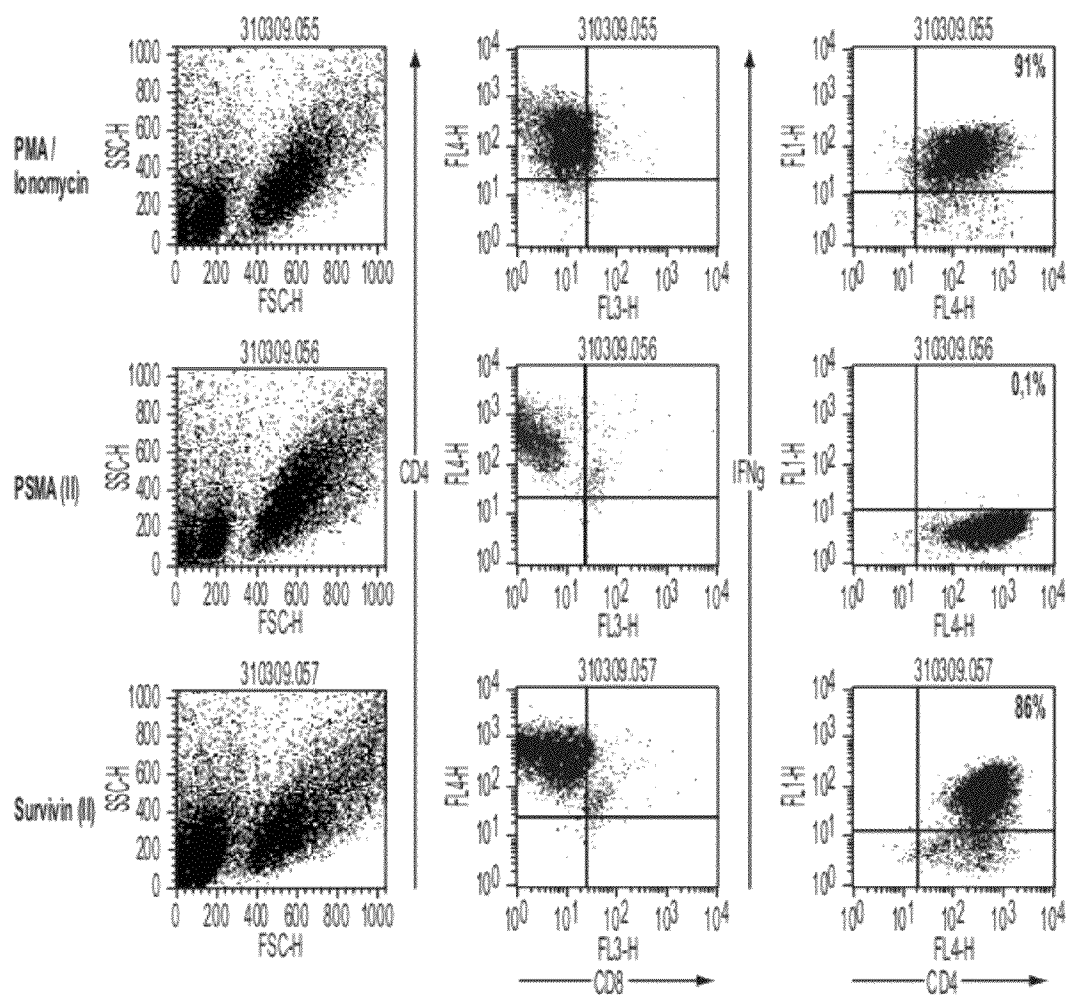
FIG. 15 shows peptide reactivity of clone Pro15_10 O. PMA/ionomycin=antigen-independent unspecific activation; Survivin (II): stimulation with the survivin 97-111 epitope; PSMA (II): stimulation with the PSMA 459-473 epitope. All reactive cells are CD4 positive.
Figure 16:
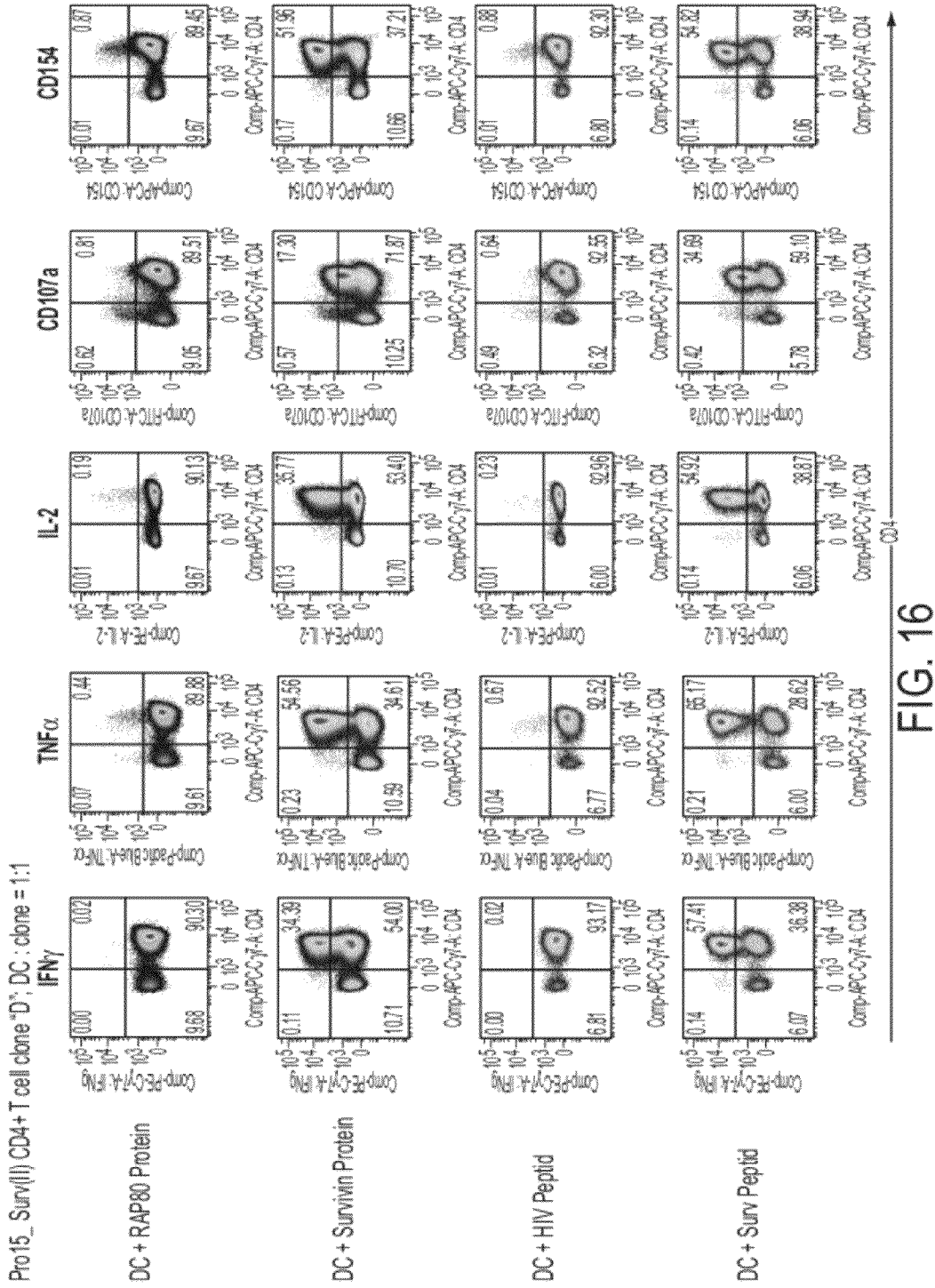
FIG. 16 characterizes the response of the CD4+ survivin-specific T-cell clone Pro15_"D" to dendritic cells primed with full-length survivin or the survivin 97-111 epitope. Immature dendritic cells incubated with recombinant survivin protein or a the survivin 97-111 epitope are recognized by survivin-specific T-cells from vaccinated patients as shown by intracellular cytokine staining. These results suggest that survivin is naturally processed by proteinases within dendritic cells and that the survivin 97-111 epitope is not destroyed by processing. In addition, these CD4+ T-cells are multifunctional as they secrete cytokines IFN-gamma, TNF-alpha and IL-2, have surface expression of CD40 ligand (CD154) and degranulate indicated by surface expression of CD107a. The indicated T-cell response is antigen-specific, as the T-cells are not activated by dendritic cells incubated with the irrelevant protein RAP80, or HIV-001 peptide.
Figure 17:
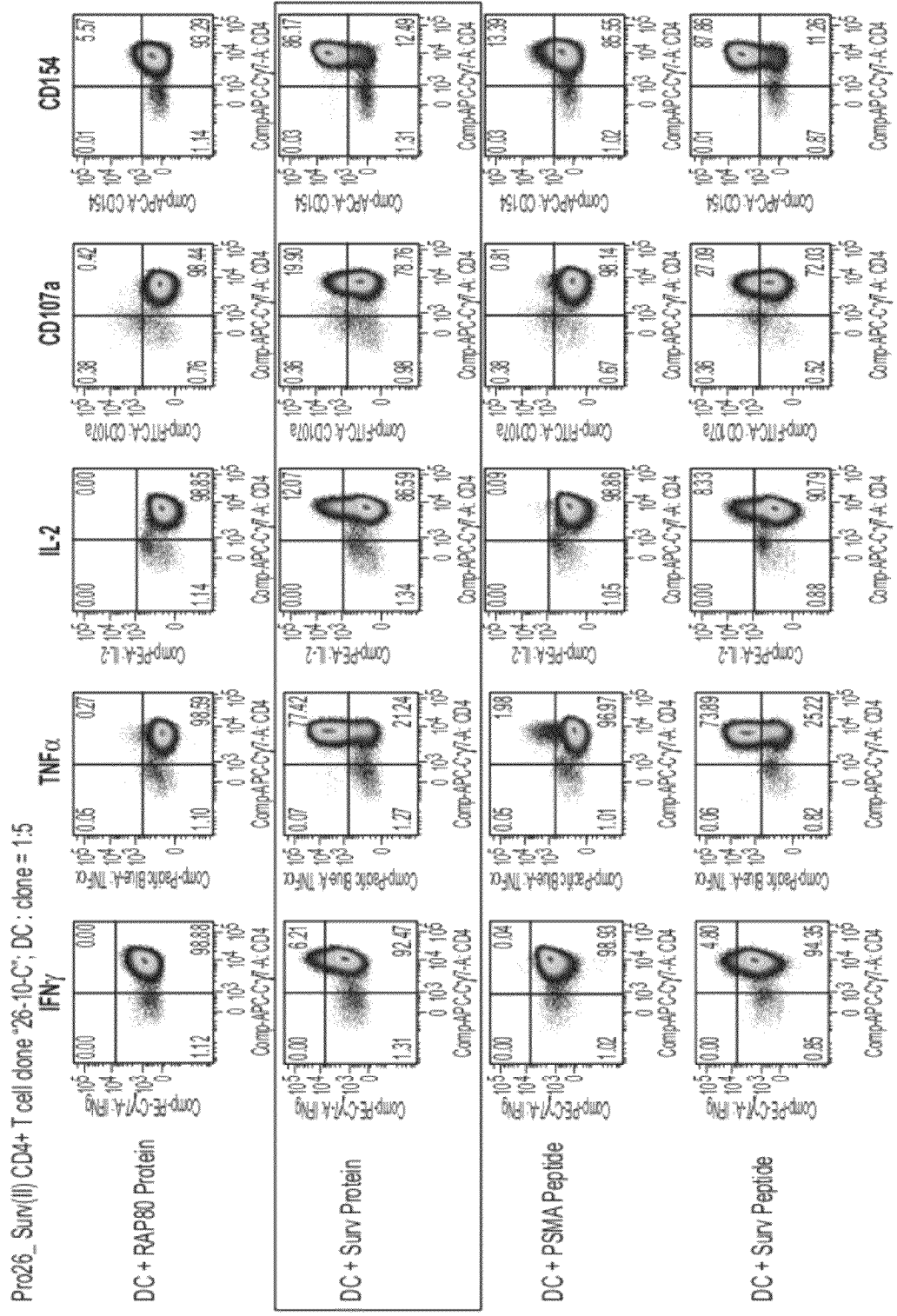
FIG. 17 shows the response of the CD4+ survivin-specific T-cell clone Pro26-10-C to dendritic cells primed with full-length survivin, survivin 97-111 epitope, or the PSMA 459-473 epitope. Immature dendritic cells incubated with recombinant survivin protein, survivin 97-111 epitope, and PSMA 459-473 epitope are recognized by antigen-specific T-cells from vaccinated patients as shown by intracellular cytokine staining. Although responsive to both survivin and PSMA epitopes, the T cell response was stronger in response to stimulation with survivin epitopes. These CD4+ T-cells are multifunctional as they secrete cytokines IFN-gamma, TNF-alpha and IL-2, have surface expression of CD40 ligand (CD154) and degranulate indicated by surface expression of CD107a. The indicated T-cell response is antigen-specific, as the T-cells are not activated by dendritic cells incubated with the irrelevant protein RAP80.
Figure 18:
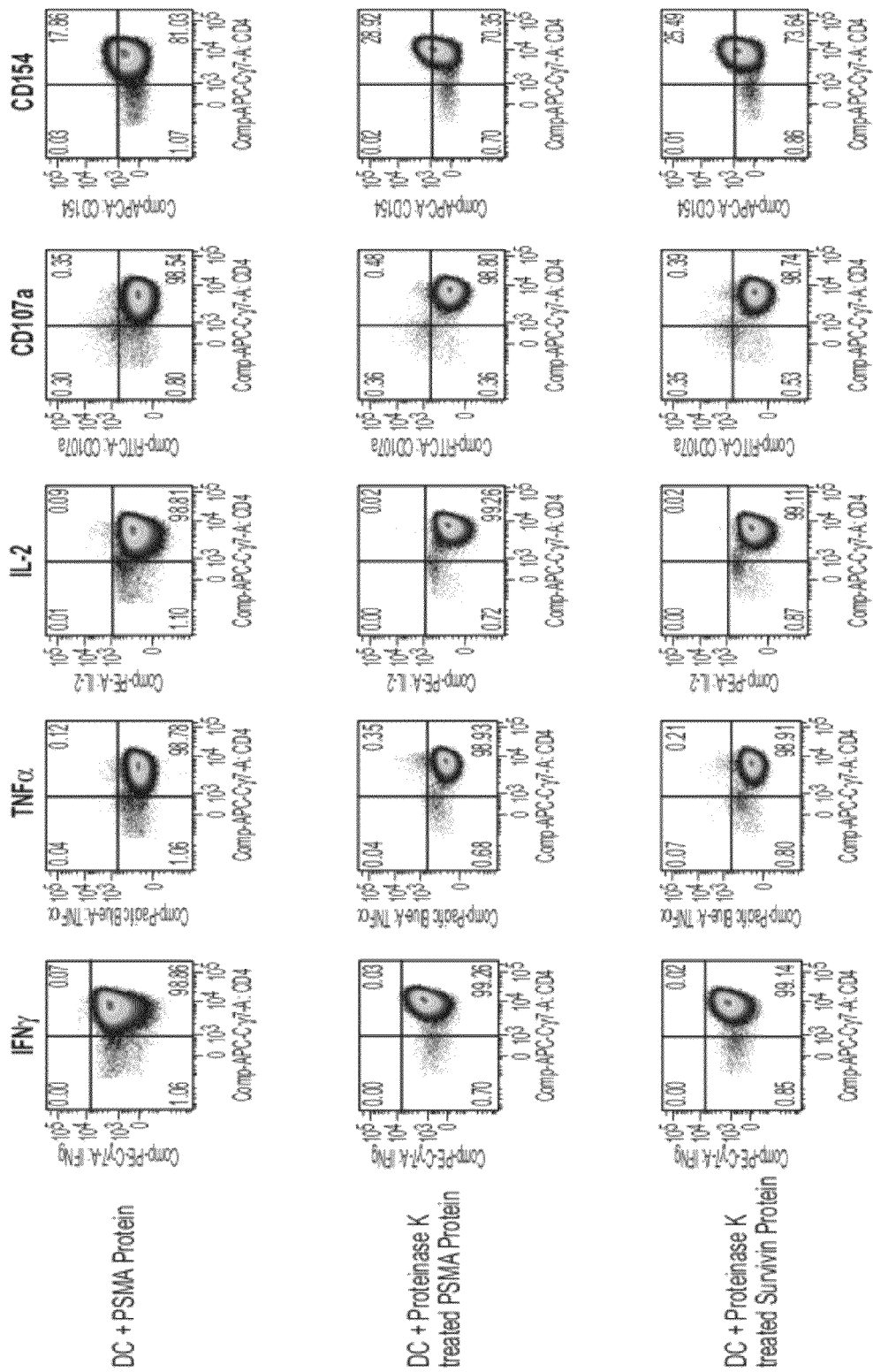
FIG. 18 shows the response of the CD4+ survivin-specific T-cell clone Pro26-10-C to dendritic cells primed with full-length PSMA protein, PSMA protein treated with proteinase K, or survivin protein treated with proteinase K.
Figure 19:
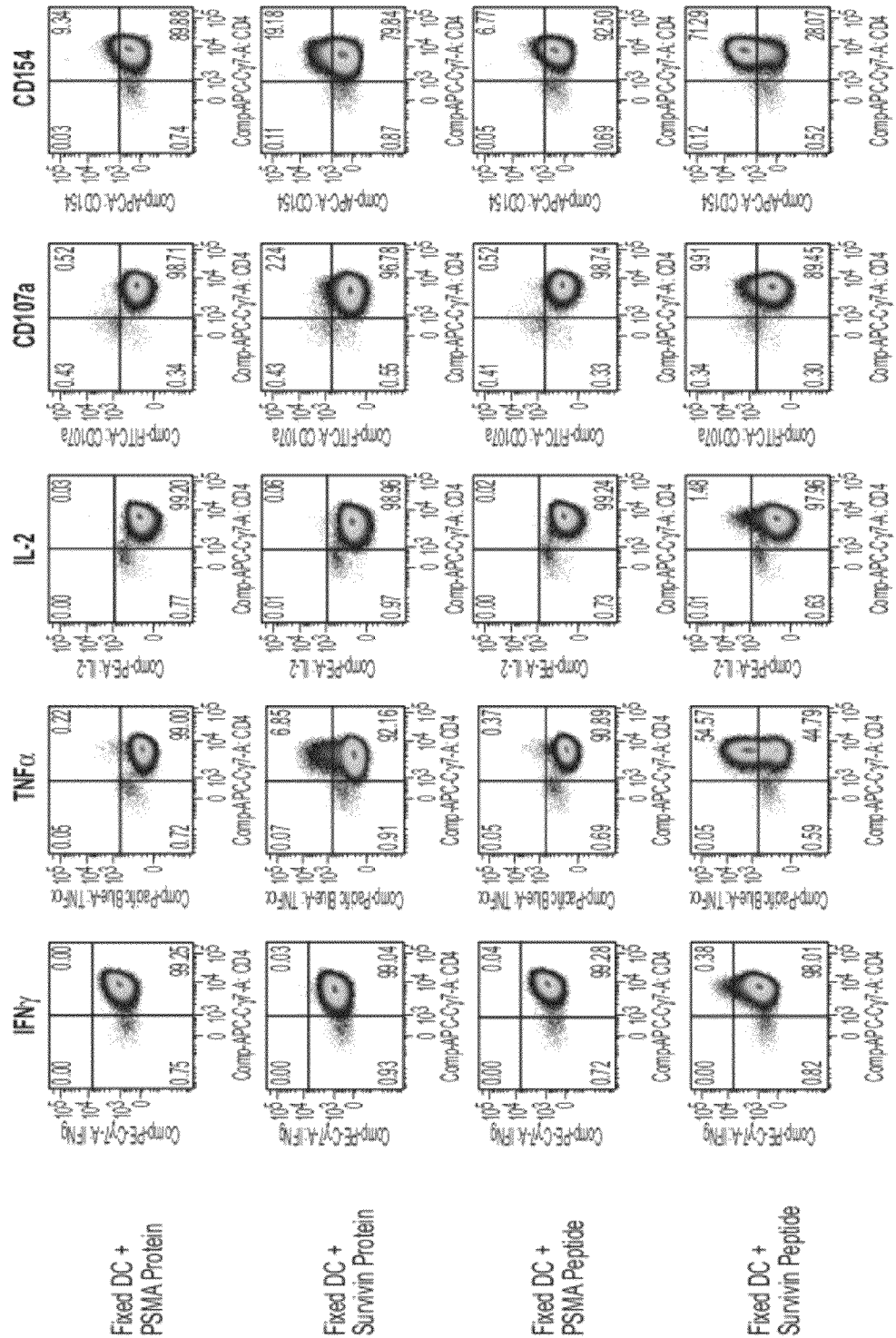
FIG. 19 shows the response of the CD4+ survivin-specific T-cell clone Pro26-10-C to fixed dendritic cells incubated with full-length survivin, survivin 97-111 epitope, full length PSMA, or the PSMA 459-473 epitope. Fixed dendritic cells incubated with survivin 97-111 epitope—but not with full-length survivin—are recognized by antigen-specific T-cells from vaccinated patients as shown by intracellular cytokine staining. This confirms that full length survivin must be cleaved by the antigen presenting cell in order to be antigenic.
Figure 20:
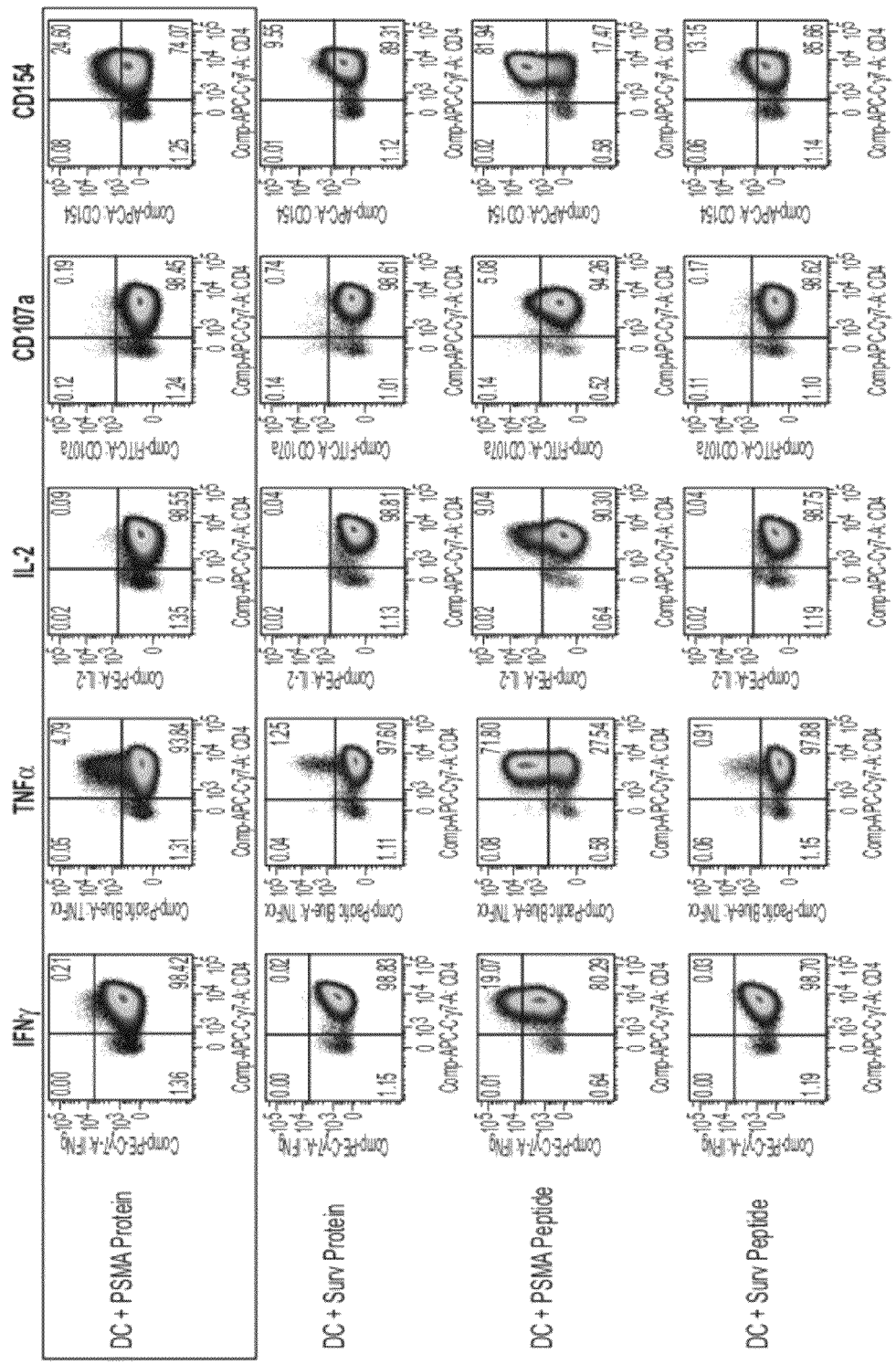
FIG. 20 shows the response of the CD4+ PSMA-specific T-cell clone Pro26-10-D to dendritic cells primed with full-length survivin, survivin 97-111 epitope, full length PSMA, or the PSMA 459-473 epitope. Immature dendritic cells incubated with PSMA 459-473 epitope are recognized by antigen-specific T-cells from vaccinated patients as shown by intracellular cytokine staining. These CD4+ T-cells are multifunctional as they secrete cytokines IFN-gamma, TNF-alpha and IL-2, have surface expression of CD40 ligand (CD154) and degranulate indicated by surface expression of CD107a. The indicated T-cell response is antigen-specific, as the T-cells are not activated by dendritic cells incubated with the survivin or the survivin 97-111 epitope.

The present disclosure relates to compositions and methods for use in manipulating the immune response to prostate cancer cells through the use of antigenic peptides that are specific for prostate tissue and/or prostate tumours.

Stimulation of an immune response is dependent upon the presence of antigens recognized as foreign by the host immune system. In recent years, various antigens that are (1) expressed specifically in prostate tissue or prostate tumors; and (2) are recognized by T-cells have successfully been identified. Such antigens are capable of stimulating T-cells and inducing antigen-specific T-cell responses to prostate cancer cells when they are expressed as a complex of HLA molecule and peptide on antigen-presenting cells (APCs), ultimately leading to tumor cell lysis. For example, various epitopes of the protein survivin have been recognized as prostate TAAs. The discovery and characterization of TAAs specific for prostate has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of CD8+ cytotoxic T-cells ("CTL") from tumor-infiltrating cell populations or from peripheral blood suggests that such cells play an important role in natural immune defenses against cancer. CD8+ T-cells in particular, which recognize class I molecules of the major histocompatibility complex (MHC)-bearing peptides of usually 8 to 10 residues derived from proteins or defect ribosomal products (DRIPS) located in the cytosol, play an important role in this response. (Schubert U, Anton L C, Gibbs J, Norbury C C, Yewdell J W, Bennink J R.; Rapid degradation of a large fraction of newly synthesized proteins by proteasomes; Nature 2000; 404(6779):770-774)).

Antigens are presented via one of two primary classes of major histocompatibility complex (MHC) molecules, MHC class I and MHC class II. In humans, MHC molecules are referred to as human leukocyte antigen ("HLA") molecules. There are two classes of MHC-molecules: MHC class I molecules that can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature. MHC class II molecules can be found predominantly on professional antigen presenting cells (APCs), and present predominantly peptides of exogenous proteins that are taken up by APCs during the course of endocytosis, and are subsequently processed. As for class I, alternative ways of antigen processing are described that allow peptides from endogenous sources to be presented by MHC class II molecules (e.g. autophagocytosis). Complexes of peptide and MHC class I molecule are recognized by CD8+ cytotoxic T-lymphocytes bearing the appropriate TCR, complexes of peptide and MHC class II molecule are recognized by CD4-positive helper T-cells bearing the appropriate TCR.

HLA class I molecules are found on every nucleated cell of the body and function to display fragments of cytosolic proteins to CD8+ cytotoxic T cells ("CTLs"). The proteins are cleaved in proteasomes, and the resulting peptides are transported out of the cytosol into the lumen of the endoplasmic reticulum and are bound to HLA class I molecules. The complex between the antigen and the HLA-class I molecule is then transported to the cell surface where the antigen can be presented to CTLs. Presentation of the antigen to CTL induces a cascade eventually leading to expansion of antigen-specific CTLs that directly kill cells have the antigen/HLA complex bound to their surface. This process occurs in every nucleated cell, thereby enabling the immune system to accurately monitor each individual cell for the presence of foreign, altered, or embryonic proteins. Although peptides presented by HLA-class I molecules typically are derived from endogenous intracellular protein molecules, there are indications that exogenous antigens taken up by the cell by macropinocytosis or phagocytosis can also be presented. Thus, an antigen-specific CTL response can be induced by immunizing the host directly with polypeptides containing an HLA-class I specific epitope.

In contrast to HLA-class I molecules, which are constitutively expressed, HLA-class II molecules are found almost exclusively on professional antigen-presenting cells, including macrophages, dendritic cells and B cells. Professional APCs endocytose extra-cellular proteins by the professional APC, digested in lysosomes, and bound by the HLA-class II molecule prior to the molecule's migration to the plasma membrane. HLA-class II-bound peptides are presented to CD4+ T helper cells ("T helper cells"). T helper cells do not have any direct cytotoxic or phagocytic activity and thus do not directly kill infected or dysfunctional host cells, but instead function by inducing or augmenting the response of other immune system components to the infected or dysfunctional cell. By way of example, activation of CD4+ T cells can lead to locally increased levels of interferon-gamma (IFNγ).

CD4-positive helper T-cells play an important role in orchestrating the effector functions of anti-tumor T-cell responses and for this reason the identification of CD4-positive T-cell epitopes derived TAAs may be of great importance for the development of pharmaceutical products for triggering anti-tumor immune responses. It has been shown in mammalian animal models that local secretion of interferon-gamma IFNγ by T helper cells can inhibit tumor development via inhibition of angiogenesis, even in the absence of CTLs. See Qin, Z. and T. Blankenstein. CD4+ T-cell-mediated tumor rejection involves inhibition of angiogenesis that is dependent on IFN gamma receptor expression by non-hematopoietic cells. Immunity. 2000, 12:677-686. Additionally, T helper cells that recognize TAAs presented by HLA class II molecules can counteract tumor progression via the induction of an antibody response (Kennedy, R. C., M. H. Shearer, A. M. Watts, and R. K. Bright. CD4+ T lymphocytes play a critical role in antibody production and tumor immunity against simian virus 40 large tumor antigen. Cancer Res. 2003, 63:1040-1045).

In contrast to HLA class I-binding TAAs, only a small number of HLA class II-binding TAAs have been described so far (www.cancerimmunity.org, www.syfpeithi.de). Since the constitutive expression of HLA class II molecules is usually limited to cells of the immune system, the possibility of isolating class II peptides directly from primary tumors was not considered possible. However, a number of MHC class II epitopes have recently been identified directly from tumors. Moreover, in tumor patients, cells of the tumor have surprisingly been found to express MHC class II molecules (EP 1642905, EP 1760088; Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170).

For a peptide to elicit a cellular immune response, it must bind to an MHC-molecule. This process is dependent on the allele of the MHC-molecule and specific polymorphisms of the amino acid sequence of the peptide. MHC-class-1-binding peptides are usually 8-10 amino acid residues in length and usually contain two conserved residues ("anchor") in their sequence that interacts with the corresponding binding groove of the MHC-molecule. In this way each MHC allele has a "binding motif" determining which peptides can bind specifically to the binding groove (Rammensee H G, Bachmann J, Stevanovic S. MHC ligands and peptide motifs, Landes Bioscience, USA, 1997).

In MHC dependent immune reaction, peptides not only have to be able to bind to certain MHC molecules expressed by tumor cells, they also have to be recognized by T-cells bearing specific T-cell receptors (TCR).

The antigens that are recognized by the tumor specific T-lymphocytes, that is, their epitopes, can be molecules derived from all protein classes, such as enzymes, receptors, transcription factors, etc. Furthermore, tumor-associated antigens, for example, can also be present in tumor cells only, for example as products of mutated genes. Another important class of tumor-associated antigens are tissue-specific antigens, such as CT ("cancer testis")-antigens that are expressed in different kinds of tumors and in healthy tissue of the testis.

Numerous TAAs have been successfully identified and characterized in recent years. Further, much research effort is expended to identify additional tumor associated antigens. Some groups of tumor-associated antigens, also referred to in the art as tumor-specific antigens, are tissue specific. Examples include, but are not limited to, tyrosinase for melanoma, PSA and PSMA for prostate cancer and chromosomal cross-overs (translocations) such as bcr/abl in lymphoma. However, many tumor-associated antigens identified occur in multiple tumor types, and some, such as oncogenic proteins and/or tumor suppressor genes (tumor suppressor genes are, for example reviewed for renal cancer in Linehan W M, Walther M M, Zbar B. The genetic basis of cancer of the kidney. J. Urol. 2003 December; 170 (6Pt1):2163-72) which actually cause the transformation event, occur in nearly all tumor types. For example, normal cellular proteins that control cell growth and differentiation, such as p53 (which is an example for a tumor suppressor gene), ras, c-met, myc, pRB, VHL, and HER-2/neu, can accumulate mutations resulting in upregulation of expression of these gene products thereby making them oncogenic (McCartey et al. Cancer Research, 1998, 15:58 2601-5; Disis et al. Ciba Found. Symp. 1994, 187:198-211). These mutant proteins can also be a target of a tumor-specific immune response in multiple types of cancer.

Effective or ineffective presentation determines the type and extent of the induced immune response, which can range from immunity to tolerance. In order to stimulate a resting, naive CTL in an antigen-specific manner, the CTL must receive two signals from the antigen-presenting cell: one via the antigen-specific T cell receptor (TCR), which interacts with an HLA/peptide complex, and a second via costimulatory factors (B7 molecules, ICAM-1, and other adhesion molecules) or cytokines (e.g., IL-2). When T lymphocytes receive only one of these signals, anergy of the T cell occurs. Tumor cells are usually poor APCs because they do not possess costimulatory molecules and often exhibit only low HLA class I expression. In addition, malignant cells often express cytokines or surface molecules that suppress an immune response directed at them. As such, the manner in which the TAA is presented to the T-cell is of considerable significance for induction of a tumor-specific immune response.

For proteins to be recognized by CTL as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, also downstream targets of the proteins directly causative for a transformation may be upregulated and thus be indirectly tumor-associated. Such indirectly tumor-associated antigens may also be targets of a vaccination approach. Essential is in both cases the presence of epitopes in the amino acid sequence of the antigen, since such peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T-cell with a corresponding TCR and the absence of tolerance for this particular epitope. T-helper cells play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

For most tumours, only few TAAs are known or they have been defined only for one particular HLA type. In contrast, numerous prostate-specific antigens and prostate carcinoma-associated antigens and peptides recognized by CTLs have successfully been identified. These TAAs are capable of stimulating T cells and inducing antigen-specific CTLs when they are expressed as a complex of HLA molecule and peptide on antigen-presenting cells.

In malignant melanoma studies, from which most experience with immunotherapy has been derived, it was shown that immunizations with one or two TAAs can lead to selection of tumor cells, thereby leading to progression of the disease during ongoing therapy with DCs. Since both types of response, CD8 and CD4 dependent, contribute jointly and synergistically to the anti-tumor effect, the identification and characterization of tumor-associated antigens recognized by either CD8+ CTLs (MHC class I molecule) or by CD4-positive CTLs (MHC class II molecule) is important in the development of tumor vaccines.

However, priming of one kind of CTL is usually insufficient to eliminate all tumor cells. Tumors are very mutagenic and thus able to respond rapidly to CTL attacks by changing their protein pattern to evade recognition by CTLs. To counter-attack the tumor evasion mechanisms a variety of specific peptides is used for vaccination. In this way a broad simultaneous attack can be mounted against the tumor by several CTL clones simultaneously. This may decrease the chances of the tumor to evade the immune response. This hypothesis has been recently confirmed in a clinical study treating late-stage melanoma patients. With only few exceptions, patients that had at least three distinct T-cell responses, showed objective clinical responses or stable disease (Banchereau et al., 2001) as well as increased survival, while the vast majority of patients with less than three T-cell responses were diagnosed with progressive disease.

Similar effects have been shown when patients suffering from renal cell carcinoma were treated with a vaccine composed of 13 different peptides (H. Singh-Jasuja, S. Walter, T. Weinschenk, A. Mayer, P. Y. Dietrich, M. Staehler, A. Stenzl, S. Stevanovic, H. Rammensee, J. Frisch; Correlation of T-cell response, clinical activity and regulatory T-cell levels in renal cell carcinoma patients treated with IMA901, a novel multi-peptide vaccine; ASCO Meeting 2007 Poster #3017; M. Staehler, A. Stenzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Poster #3017).

The major task in the development of a tumor vaccine is therefore not only the identification and characterization of novel tumor associated antigens and immunogenic T-helper epitopes derived thereof, but also the combination of different epitopes to increase the likelihood of a response to more than one epitope for each patient.

Compositions are thus provided comprising at least one HLA-binding peptide comprising, consisting essentially of, or consisting of an epitope derived from a prostate-associated antigenic molecule.

As used herein, the phrase "HLA-binding peptide" refers to any polypeptide that is capable of being bound by a human leukocyte antigen molecule of HLA class I or HLA class II.

As used herein, the term "epitope" shall refer to an amino acid sequence that is sufficient to permit the molecule in which it is contained to be bound by a human leukocyte antigen molecule of HLA class I or HLA class II. Methods for identifying epitopes are known in the art. These methods include, but are not limited to: (a) gene expression analysis using an individual patient's T-cells, see van der Bruggen et al., A gene encoding an antigen recognized by cytolytic T lymphocytes on a human melanoma, Science 1991; 254 (5038):1643-1647; (b) mass spectrometric sequencing of tumour associated peptides, Cox et al., Identification of a peptide recognized by five melanoma-specific human cytotoxic T cell lines, Science 1994; 264(5159):716-719; and (c) "reverse immunology," wherein known TAAs are used to predict epitopes according to allele-specific peptide motifs, see Stevanovic, Identification of tumor-associated T-cell epitopes for vaccine development, Nat. Rev. Cancer 2002; 2(7):514-520; Celis et al., Induction of anti-tumor cytotoxic T lymphocytes in normal humans using primary cultures and synthetic peptide epitopes, Proc. Nat'l Acad. Sci. USA 1994; 91(6):2105-2109.

As used herein, the term "prostate-associated antigenic molecule" shall refer to any epitope-containing molecule that is differentially expressed in either (a) prostate tissue; or (b) prostate cancer cells. Exemplary prostate-associated antigenic molecules include: prostate specific antigen, prostate stem cell antigen, prostate specific membrane antigen, survivin, prostein, and transient receptor potential-p8. Exemplary epitopes derived from these prostate-associated antigenic molecules are shown at FIG. 1. However, any epitope derived from any prostate-associated antigenic molecule may be used.

The HLA-binding peptides disclosed herein can be modified by the substitution of one or more residues at different, possibly selective, sites within the peptide chain, if not otherwise stated. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement.

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides disclosed and shall be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present disclosure.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

In another aspect, compositions are provided comprising at least two HLA-binding peptides wherein at least one of the HLA-binding peptides is an HLA-class I peptide and at least one of the HLA-binding peptides is an HLA class II peptide.

As used herein, the phrase "HLA class I peptide" shall refer to any polypeptide comprising an epitope that is capable of, or predicted to be capable of, being bound by a human leukocyte antigen molecule of HLA class I. By way of example, "HLA class I peptides" include HLA-A2-restricted peptides, which bind to specific alleles of the HLA-A2 serotype, including, but not limited to, HLA-A2 serotype molecules having HLA-A*0201, *0202, *0203, *0206, or *0207 alpha-chains. Exemplary "HLA-class I peptides" are SEQ ID NO:1, SEQ ID NO:2, SEQ ID NO: 3, SEQ ID NO: 4, SEQ ID NO:5, SEQ ID NO:6, SEQ ID NO:7, SEQ ID NO:8, SEQ ID NO:9, SEQ ID NO:10, SEQ ID NO: 11, each of which is an HLA-A*201-restricted peptide.

The present disclosure further provides peptides that stem from antigens associated with tumorigenesis, and have the ability to bind sufficiently to MHC(HLA) class II molecules for triggering an immune response of human leukocytes, especially lymphocytes, especially T lymphocytes, especially CD4-positive T lymphocytes, especially CD4-positive T lymphocytes mediating $T_{H1}$-type immune responses. As used herein, the phrase "HLA class II peptide" shall refer to any polypeptide comprising an epitope that is capable of, or predicted to be capable of, being bound by a human leukocyte antigen molecule of HLA class II. Exemplary "HLA class II peptides" are listed at FIG. 1 as SEQ ID NO: 13 and SEQ ID NO: 14.

Further peptides of the invention are:

| Sequence | Gene symbol | HLA binding | SEQ ID NO |
|---|---|---|---|
| DFIATLGKLSGLHG | ACPP | Class II | 15 |
| ATVLFGIAR | ABCC4 | HLA-A*11 | 16 |
| AVCGGVLVHP | KLK3 | HLA-C | 17 |
| AVCGGVLVHPQ | KLK3 | HLA-C | 18 |
| DQLBFLERA | FOLH1B | HLA-A*23, HLA-B*39 | 19 |
| DYNFVFTSF | AMD1 | HLA-A*24 | 20 |
| EVIGHYPGSSF | PMEPA1 | HLA-B*41, HLA-B*51 and/or HLA-C | 21 |
| EVITGIRII | ABCC4 | HLA-B*41, -B*51 and/or -C | 22 |
| LLPPPPLLA | ASTN2 | HLA-A*02 | 23 |
| NADPQAVTM | MAGED2 | HLA-A*02 | 24 |
| NYEETFPHI | MUC6 | HLA-A*24 | 25 |
| SESDTIRSI | KLK4 | HLA-B*44 | 26 |
| SVVGGFVSHY | MYO6 | HLA-B*41, HLA-C | 27 |
| SYPYYPYLY | NKX3-1 | HLA-C | 28 |
| TIIDSDKIMVL | ABCC4 | HLA-C | 29 |
| TYDFAHCTF | Not assigned | HLA-C | 30 |
| VFDTAIAHLF | SIAH2 | HLA-A*24 | 31 |
| VYNPTPNSL | COL12A1 | HLA-A*24 and HLA-A*11 and/or HLA-B*35 | 32 |
| YTIGLGLHSL | KLK4 | HLA-B*41, HLA-B*51, and/or HLA-C | 33 |
| Further optional peptides of the invention are | | | |
| APLLLARAA | ACPP | HLA-C | 34 |
| KRATQIPSY | ACPP | B*2705 | 35 |
| MRAAPLLL | ACPP | class I | 36 |
| MRAAPLLLA | ACPP | class I | 37 |

It is known that HLA-class II peptides are composed of a "core sequence" having a certain HLA-specific amino acid motif and, optionally, N- and/or C-terminal extensions which do not interfere with the function of the core sequence (i.e. are deemed as irrelevant for the interaction of the peptide and the T-cell). The N- and/or C-terminal extensions can, for example, be between 1 to 10 amino acids in length, respectively. These peptide can be used either directly to load HLA class II molecules or the sequence can be cloned into the vectors according to the description herein below. As these peptides form the final product of the processing of larger peptides within the cell, longer peptides can be used as well. The HLA-class II peptides disclosed herein may be of any size, including but not limited to having a size of less than 100,000 Dalton in molecular weight, less than 50,000 Dalton in molecular weight, less than 10,000 Dalton in molecular weight, less than 5,000 Dalton in molecular weight, less than 2,500 Dalton in molecular weight, or from about 1000 to 2000 Dalton in molecular weight. In terms of the number of amino acid residues, the peptides of the disclosure may, by way of example and not exclusion, have fewer than 1000 residues, fewer than 500 residues, or fewer than 100 residues.

Accordingly, compositions of peptides and variants thereof are disclosed wherein the peptide or variant has an overall length of from 8 to 100, 8 to 60 amino acids, from 8 to 30, and from 8 to 17, or wherein the peptide or variant has 8, 9, 10, 11, 12, 13, 14, 15 or 16 amino acids. In another aspect, the peptides have a core sequence selected from a group consisting of SEQ ID NO: 13 and SEQ ID NO: 14 with extensions of 1 to 10 amino acids on the C-terminal and/or the N-terminal, wherein the overall number of these flanking amino acids is 1 to 12, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to 10, or 10 to 12, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide.

It is also possible that MHC class I epitopes, although usually from 8 to 10 amino acids long, are generated by peptide processing from longer peptides or proteins that include the actual epitope. Similar to MHC class II epitopes, the flanking residues of elongated precursor peptides upstream and/or downstream of the N- and C-terminus of the actual epitope may be chosen so that they neither substantially affect the presentation of the peptide to the CTL nor mask the sites for proteolytic cleavage necessary to yield the actual epitope mediated by processing of the elongated peptide.

Thus, in another aspect, the peptides have a core sequence consisting of SEQ ID NO: 1 to SEQ ID NO: 11 and SEQ ID NO: 15 to SEQ ID NO: 37 with extensions of 1 to 10 flanking amino acids on the C-terminal and/or the N-terminal. In a further aspect, the overall number of these flanking amino acids is 1 to 12, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to 10, or 10 to 12, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the of SEQ ID NO: 1 to SEQ ID NO: 12, and SEQ ID NO: 15 to SEQ ID NO: 40.

In a further aspect, the present disclosure provides peptides and variants of MHC class I epitopes having an overall length from 8 to 100 amino acids, from 8 to 60 amino acids, from 8 to 30 amino acids, and from 8 to 18 amino acids, or having 8, 9, 10, 11, 12, 13, 14, 15, 16 or 17 amino acids.

Of course, the disclosed peptide or variant will have the ability to bind to a molecule of the human MHC class I or II. Binding of a peptide or a variant to a MHC complex may be tested by methods known in the art, for example those described in the examples of the present disclosure below or those described in the literature for different MHC class II alleles (e.g. Vogt A B, Kropshofer H, Kalbacher H, Kalbus M, Rammensee H G, Coligan J E, Martin R; Ligand motifs of HLA-DRB5*0101 and DRB1*1501 molecules delineated from self-peptides; J Immunol. 1994; 153(4):1665-1673; Malcherek G, Gnau V, Stevanovic S, Rammensee H G, Jung G, Melms A; Analysis of allele-specific contact sites of natural HLA-DR17 ligands; J Immunol. 1994; 153(3):1141-1149; Manici S, Sturniolo T, Imro M A, Hammer J, Sinigaglia F, Noppen C, Spagnoli G, Mazzi B, Bellone M, Dellabona P, Protti M P; Melanoma cells present a MAGE-3 epitope to CD4(+) cytotoxic T cells in association with histocompatibility leukocyte antigen DR11; J Exp Med. 1999; 189(5): 871-876; Hammer J, Gallazzi F, Bono E, Karr R W, Guenot J, Valsasnini P, Nagy Z A, Sinigaglia F; Peptide binding specificity of HLA-DR4 molecules: correlation with rheumatoid arthritis association; J Exp Med. 1995 181(5):1847-1855; Tompkins S M, Rota P A, Moore J C, Jensen P E; A europium fluoro-immunoassay for measuring binding of antigen to class II MHC glycoproteins; J Immunol Methods. 1993; 163 (2): 209-216; Boyton R J, Lohmann T, Londei M, Kalbacher H, Halder T, Frater A J, Douek D C, Leslie D G, Flavell R A, Altmann D M; Glutamic acid decarboxylase T lymphocyte responses associated with susceptibility or resistance to type I diabetes: analysis in disease discordant human twins, non-obese diabetic mice and HLA-DQ transgenic mice; Int Immunol. 1998 (12):1765-1776).

Additional N- and/or C-terminally located stretches of amino acids that are not necessarily forming part of the peptide that functions as the actual epitope for MHC molecules but may, nevertheless, be important to provide for an efficient introduction of the peptide according to the present disclosure into the cells. In one embodiment, the peptide of the present disclosure is a fusion protein which comprises, for example, the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984)).

In another aspect, the peptides have an overall length of from 8 to 100 amino acids, 8 to 60 amino acids, from 8 to 30 amino acids, and from 8 to 17 amino acids, or having 9, 10, 11, 12, 13, 14, 15, or 16 amino acids.

In addition, the peptide or variant may be modified further to improve stability and/or binding to MHC molecules to elicit a stronger immune response. Methods for such an optimization of a peptide sequence are well known in the art and include, for example, the introduction of reverse peptide bonds or non-peptide bonds.

Thus, according to another aspect the disclosure provides a composition, wherein at least one peptide or variant includes non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC and T helper cell responses, these pseudopeptides are useful. Retro-inverse peptides, containing NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains that involves polypeptides synthesized by standard procedures and the non-peptide bond synthesized by reacting an amino aldehyde and an amino acid in the presence of NaCNBH₃.

Peptides comprising the sequences of the disclosure described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, e.g. the hydrophobic group, t-butyloxycarbonyl, or an amido group may be added to the peptides' carboxy termini.

Further, all peptides of the disclosure may be synthesized to alter their steric configuration. For example, the D-isomer of one or more of the amino acid residues of the peptide may be used, rather than the usual L-isomer. Still further, at least one of the amino acid residues of the peptides of the disclosure may be substituted by one of the well known non-naturally occurring amino acid residues. Alterations such as these may serve to increase the stability, bioavailability and/or binding action of the peptides of the disclosure.

Similarly, a peptide or variant of the disclosure may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

Generally, peptides and variants (at least those containing peptide linkages between amino acid residues) may be synthesized e.g. using the Fmoc-polyamide mode of solid-phase peptide synthesis as disclosed by Lu et al (1981) J. Org. Chem. 46, 3433 and references therein.

Purification may be effected by any one, or a combination of, techniques such as recrystallisation, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the disclosure provides a nucleic acid (e.g. polynucleotide) encoding one of the disclosed peptides or variants. The polynucleotide may be e.g. DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. Of course, it is only peptides containing naturally occurring amino acid residues joined by naturally occurring peptide bonds are encodable by a polynucleotide. A still further aspect of the disclosure provides an expression vector capable of expressing a polypeptide according to the disclosure. Expression vectors for different cell types are well known in the art and can be selected without undue experimentation.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques that are well known in the art.

In one embodiment, the composition comprises at least two peptides consisting essentially of amino acid sequences according to SEQ ID NO: 1 to SEQ ID NO: 11, and SEQ ID NO: 13 to SEQ ID NO: 40.

In another embodiment, the composition comprises at least two peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 40.

In another embodiment, the composition comprises at least four peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 40.

In another embodiment, the composition comprises ten peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 40.

In another embodiment, the composition comprises at least two peptides, at least four peptides, or at least ten peptides, said peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02.

In another embodiment, the composition comprises at least two peptides, at least four peptides, or at least ten peptides, said peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide is selected according to the HLA set of the subject to be treated.

In one embodiment, the composition comprises at least two peptides consisting of amino acid sequences according to SEQ ID NO: 1 to SEQ ID NO: 11 and SEQ ID NO: 13 to SEQ ID NO: 42.

In another embodiment, the composition comprises at least two peptides consisting of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 42.

In another embodiment, the composition comprises at least four peptides consisting of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 42.

In another embodiment, the composition comprises ten peptides consisting of amino acid sequences according to SEQ ID NO: 1, SEQ ID NO: 2; SEQ ID NO: 5, SEQ ID NO: 7, SEQ ID NO: 9 to SEQ ID NO: 11, and SEQ ID NO: 13 to SEQ ID NO: 42.

In another embodiment, the composition comprises at least 2 peptides, at least 4 peptides, or at least 10 peptides, said peptides consisting of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02.

In another embodiment, the composition comprises at least 2 peptides, at least 4 peptides, or at least 10 peptides, said peptides consisting of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide is selected according to the HLA set of the subject in need.

In one embodiment, the composition comprises at least two peptides consisting essentially of amino acid sequences according to SEQ ID NO: 1 to SEQ ID NO: 11, and SEQ ID NO: 13 to SEQ ID NO: 14, and SEQ ID NO: 15 to SEQ ID NO: 31.

In another embodiment, the composition comprises at least two peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32.

In another embodiment, the composition comprises at least four peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32.

In another embodiment, the composition comprises ten peptides consisting essentially of amino acid sequences according to and selected from a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32.

In another embodiment, the composition comprises at least two peptides, at least four peptides, or at least ten peptides, said peptides consisting essentially of amino acid sequences according to and selected from a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02.

In another embodiment, the composition comprises at least two peptides, at least four peptides, or at least ten peptides, said peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide is selected according to the HLA set of the subject to be treated.

In one embodiment for HLA-A*02, the composition comprises at least one peptide consisting of amino acid sequences according to SEQ ID: 23 and SEQ ID: 24, and at least one peptide consisting of amino acid sequences according to SEQ ID NO: 1 to SEQ ID NO: 11, and SEQ ID NO: 13 to SEQ ID NO: 14.

In one embodiment for HLA-A*02, the composition comprises at least one peptide consisting of amino acid sequences according to SEQ ID: 23 and SEQ ID: 24 and SEQ ID NO: 1, SEQ ID NO: 2; SEQ ID NO: 5, SEQ ID NO: 7, SEQ ID NO: 9 to SEQ ID NO: 11, SEQ ID NO: 13, and SEQ ID NO: 14.

In one embodiment for HLA-A*02, the composition comprises at least one peptide consisting of amino acid sequences according to SEQ ID: 23, and SEQ ID: 24, and SEQ ID NO: 1, SEQ ID NO: 2; SEQ ID NO: 5, SEQ ID NO: 7, SEQ ID NO: 9 to SEQ ID NO: 11, SEQ ID NO: 13, and SEQ ID NO: 14.

In another embodiment for HLA-A*02, the composition comprises ten peptides consisting of amino acid sequences according to SEQ ID: 23, and SEQ ID: 24, and SEQ ID NO:

1, SEQ ID NO: 2; SEQ ID NO: 5, SEQ ID NO: 7, SEQ ID NO: 9 to SEQ ID NO: 11, SEQ ID NO: 13, and SEQ ID NO: 14.

In another embodiment for HLA-A*02, the composition comprises at least two peptides, at least four peptides, or at least ten peptides, said peptides consisting of amino acid sequences according to SEQ ID: 23 and SEQ ID: 24 and SEQ ID NO: 1, SEQ ID NO: 2; SEQ ID NO: 5, SEQ ID NO: 7, SEQ ID NO: 9 to SEQ ID NO: 11, SEQ ID NO: 13, and SEQ ID NO: 14, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02.

In another embodiment HLA-A*02, the composition comprises at least two peptides, at least four peptides, or at least ten peptides, said peptides consisting of amino acid sequences according to SEQ ID: 23 and SEQ ID: 24, and SEQ ID NO: 1, SEQ ID NO: 2; SEQ ID NO: 5, SEQ ID NO: 7, SEQ ID NO: 9 to SEQ ID NO: 11, SEQ ID NO: 13, and SEQ ID NO: 14, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide is selected according to the HLA set of the subject in need.

In one embodiment for HLA-A*24 in combination with HLA-A*02, the composition comprises at least two peptides consisting essentially of amino acid sequences according to SEQ ID NO: 20, SEQ ID NO: 25, SEQ ID NO: 31 and SEQ ID NO: 32, and a group consisting of SEQ ID NO: 1 to SEQ ID NO: 11 and SEQ ID NO: 13 or SEQ ID NO: 14.

In another embodiment for HLA-A*24 in combination with HLA-A*02, the composition comprises at least two different peptides consisting essentially of amino acid sequences according to SEQ ID NO: 20, SEQ ID NO: 25, SEQ ID NO: 31 and SEQ ID NO: 32 and a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32.

In another embodiment for HLA-A*24 in combination with HLA-A*02, the composition comprises at least two different peptides consisting essentially of amino acid sequences according to SEQ ID NO: 20, SEQ ID NO: 25, SEQ ID NO: 31 and SEQ ID NO: 32 and a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31 and SEQ ID NO:32.

In another embodiment, the composition comprises ten peptides consisting essentially of amino acid sequences according to and selected from a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31 and SEQ ID NO:32.

In another embodiment, the composition comprises at least 2 peptides, at least 4 peptides, or at least 10 peptides, said peptides consisting essentially of amino acid sequences according to and selected from a group consisting of SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02.

In another embodiment, the composition comprises at least 2 peptides, at least 4 peptides, or at least 10 peptides, said peptides consisting essentially of amino acid sequences according to SEQ ID NO: 1, SEQ ID NO: 2; SEQ ID NO: 5, SEQ ID NO: 7, SEQ ID NO: 9 to SEQ ID NO: 11, SEQ ID NO: 13, SEQ ID NO: 14, SEQ ID NO:23, SEQ ID NO:24, SEQ ID NO:25, SEQ ID NO:20, SEQ ID NO:31, and SEQ ID NO:32, and at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide is selected according to the HLA set of the subject to be treated.

In one embodiment, the composition comprises at least two peptides consisting of amino acid sequences according to SEQ ID NO: 20, SEQ ID NO: 23 to SEQ ID NO: 25, SEQ ID NO: 31 and SEQ ID NO: 32, SEQ ID NO: 1 to SEQ ID NO: 11 and SEQ ID NO: 13 to SEQ ID NO: 14 and at least one additional peptide according to SEQ ID NO: 15 to SEQ ID 19, SEQ ID:21, SEQ ID NO:22, SEQ ID NO: 26 to SEQ ID NO:30 and SEQ ID NO:33, wherein the additional peptide/s is/are selected according to the HLA set of the subject to be treated and optionally at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide/s is/are selected according to the HLA set of the subject to be treated.

In another embodiment, the composition comprises at least two peptides consisting of amino acid sequences according to SEQ ID NO: 20, SEQ ID NO: 23 to SEQ ID NO: 25, SEQ ID NO: 31 and SEQ ID NO: 32 SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one additional peptide according to SEQ ID NO: 15 to SEQ ID 19, SEQ ID:21, SEQ ID NO:22, SEQ ID NO: 26 to SEQ ID NO:30 and SEQ ID NO:33, wherein the additional peptide/s is/are selected according to the HLA set of the subject in need, and, optionally, at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide/s is/are selected according to the HLA set of the subject to be treated.

In another embodiment, the composition comprises at least four peptides consisting of amino acid sequences according to SEQ ID NO: 20, SEQ ID NO: 23 to SEQ ID NO: 25, SEQ ID NO: 31 and SEQ ID NO: 32, SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one additional peptide according to SEQ ID NO: 15 to SEQ ID NO: 19, SEQ ID:21, SEQ ID NO:22, SEQ ID NO: 26 to SEQ ID NO:30, and SEQ ID NO:33, wherein the additional peptide/s is/are selected according to the HLA set of the subject to be treated, and optionally at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide/s is/are selected according to the HLA set of the subject to be treated.

In another embodiment, the composition comprises ten peptides consisting of amino acid sequences according to EQ ID NO: 20, SEQ ID NO: 23 to SEQ ID NO: 25, SEQ ID NO: 31 and SEQ ID NO: 32, SEQ ID NO: 1, SEQ ID NO: 2; SEQ ID NO: 5, SEQ ID NO: 7, SEQ ID NO: 9 to SEQ ID NO: 11, SEQ ID NO: 13 and SEQ ID NO: 14 and at least one additional peptide according to SEQ ID NO: 15 to SEQ ID NO: 19, SEQ ID:21, SEQ ID NO:22, SEQ ID NO: 26 to SEQ ID NO:30, and SEQ ID NO:33, wherein the additional peptide/s is/are selected according to the HLA set of the subject in need and optionally at least one peptide selected from the group consisting of SEQ ID NO: 38 BIR-002b FTELTLGEF derived from Survivin HLA-A1, SEQ ID NO: 39 BIR-002c LMLGEFLKL derived from Survivin HLA-A2, SEQ ID NO: 40 BIR-002d EPDLAQCFY derived from Survivin HLA-B35, BIR-002a SEQ ID NO: 41 TLGEFLKLDRERAKD derived from Survivin HLA-DR, and BIR-004 SEQ ID NO:42 ELTLGEFLKLDRERAKN derived from Survivin HLA-DR and HLA-A*02, wherein the additional peptide/s is/are selected according to the HLA set of the subject to be treated.

WO 2004/067023 describes MHC Class I-restricted peptides derived from the tumor associated antigen survivin, which peptides are capable of binding to Class I HLA molecules at a high affinity.

The optimum amount of each peptide to be included in the vaccine and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. By way of example and not limitation, peptide injection may be performed s.c., i.d., i.p., i.m., and i.v. By way of example and not limitation, DNA injection may be performed i.d., i.m., s.c., i.p. and i.v. Doses of e.g. 1 to 500 mg, 50 μg and 1.5 mg, or 125 μg to 500 μg, of peptide or DNA may be given and will depend from the respective peptide or DNA. Doses of this range were successfully used in previous trials (Brunsvig P F, Aamdal S, Gjertsen M K, Kvalheim G, Markowski-Grimsrud C J, Sve I, Dyrhaug M, Trachsel S, Møller M, Eriksen J A, Gaudernack G; Telomerase peptide vaccination: a phase I/II study in patients with non-small cell lung cancer; Cancer Immunol Immunother. 2006; 55(12):1553-1564; M. Staehler, A. Stenzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Abstract No 3017).

The composition disclosed herein may be compiled such that the selection, number and/or amount of peptides present in the composition is/are tissue, cancer, and/or patient-specific. For instance the exact selection of peptides can be guided by expression patterns of the parent proteins in a given tissue to avoid side effects. The selection may be dependent from the specific type of cancer that the patient to be treated is suffering from as well as the status of the disease, earlier treatment regimens, the immune status of the patient, and, of course, the HLA-haplotype of the patient. Furthermore, the vaccine according to the disclosure can contain individualized components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analyzing the IFN-gamma production (see also examples below). Usually, the most efficient peptides are then combined as a vaccine for the purposes as described above.

A suitable vaccine may contain 2, 3, 4, 5, 6, 7, 8, 9, 10, 11, 12, 13, 14, 15, 16, 17, 18, 19, or 20 different peptides. The length of the peptide for use in a cancer vaccine may be any suitable peptide. In particular, it may be a suitable 9-mer peptide or a suitable 8-mer or 9-mer or 10-mer or 11-mer peptide or 12-mer, 13-mer, 14-mer or 15-mer. Longer peptides may also be suitable, 9-mer or 10-mer peptides as described in the attached Tables 1 and 2 are preferred for MHC class I-peptides, while 12- to 15-mers are preferred for MHC class II peptides.

The peptide(s) constitute(s) a tumor or cancer vaccine. It may be administered directly into the patient, into the affected organ or systemically, or applied ex vivo to cells derived from the patient or a human cell line which are subsequently administered to the patient, or used in vitro to select a sub-population from immune cells derived from the patient, which are then re-administered to the patient.

The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides whose sequence is given are expected to stimulate CD4 T cells or CD8 CTL. However, stimulation is more efficient in the presence of help provided by T-cells positive for the opposite CD. Thus, for MHC Class II epitopes which stimulate CD4 T cells the fusion partner or sections of a hybrid molecule suitably provide epitopes which stimulate CD8-positive T-cells. On the other hand, for MHC Class I epitopes which stimulate CD8 CTL, the fusion partner or sections of a hybrid molecule suitably provide epitopes which stimulate CD4-positive T cells. CD4- and CD8-stimulating epitopes are well known in the art and include those identified in the present disclosure.

Pharmaceutically acceptable carriers are well known and are usually liquids, in which an active therapeutic agent is formulated. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, Md.: Lippincott Williams & Wilkins, 2000 and include, but are not limited to, saline, water, buffered water, 0.3% glycine, hyaluronic acid, dextrose and the like. Recently, it was found that certain fat emulsions, which have been in use for many years for intravenous nutrition of human patients, can also act as a vehicle for peptides. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

In order to elicit an immune response it is usually necessary to include adjuvants that render the composition more immunogenic. In a further aspect, compositions are provided comprising at least one HLA-binding peptide and an immunological adjuvant, wherein the HLA-binding peptide comprises an epitope derived from a prostate-associated antigenic molecule.

As used herein, the term "immunological adjuvant" shall refer to any substance that non-specifically accelerates, prolongs, or otherwise enhances antigen-specific immune responses when used in combination with antigenic molecules. Immunological adjuvants are well known in the art and any immunological adjuvant may be used. Suitable adjuvants include, but are not limited to 1018 ISS, aluminum salts, Amplivax®, AS15, BCG, CP-870,893, CpG7909, CyaA, Mologen's dSLIM®, GM-CSF, IC30, IC31, Imiquimod®, ImuFact IMP321, interferon-alpha or -beta, IS Patch, ISS, ISCOMs, JuvImmune®, LipoVac®, MF59, monophosphoryl lipid A, and other non-toxic LPS derivatives, Montanide IMS1312, Montanide ISA 206, Montanide ISA 50V, Montanide ISA-51, OK-432, OM-174, OM-197-MP-EC, ONTAK, PepTel® vector system, PLG microparticles, Resiquimod®, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox, Quil or Superfos®. Adjuvants such as Imiquimod®, Resimiquimod®, incomplete Freund's, interferon-alpha or GM-CSF are preferred. Several immunological adjuvants (e.g., MF59) specific for dendritic cells and their preparation have been described previously (Dupuis M, Murphy T J, Higgins D, Ugozzoli M, van Nest G, Ott G, McDonald D M; Dendritic cells internalize vaccine adjuvant after intramuscular injection; Cell Immunol. 1998; 186(1):18-27; Allison A C; The mode of action of immunological adjuvants; Dev Biol Stand. 1998; 92:3-11). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, Cunningham H T, Carbone D P; IL-12 and mutant P53 peptide-pulsed dendritic cells for the specific immunotherapy of cancer; J Immunother Emphasis Tumor Immunol. 1996 (6):414-418).

CpG immunostimulatory oligonucleotides have also been reported to enhance the effects of adjuvants and act as adjuvants themselves in a vaccine setting. Without bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Therapeutic potential of Toll-like receptor 9 activation, Nature Reviews, Drug Discovery, 2006, 5, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM® (double Stem Loop Immunomodulator) by Mologen (Berlin, Germany). Other TLR binding molecules such as RNA binding TLR 7, TLR 8 and/or TLR 9 may also be used.

Other examples for useful adjuvants include, but are not limited to chemically modified CpGs (e.g. CpR, Idera), mucin-1-mRNA/protamine complex, Poly(I:C) (e.g. polyI: C12U), non-CpG bacterial DNA or RNA as well as immunoactive small molecules and antibodies such as imidazoquinolines, cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab and SC58175, which may act therapeutically and/or as an adjuvant. The amounts and concentrations of adjuvants and additives useful in the context of the present disclosure can readily be determined by the skilled artisan without undue experimentation.

In one embodiment, the adjuvant is selected from the group consisting of dSLIM®, BCG, OK432, imiquimod, mucin-1-mRNA/protamine complex, resimiquimod, GM-CSF, interferon-alpha, PeviTer® and JuvImmune® or combinations thereof.

In another embodiment the adjuvant is selected from the group consisting of colony-stimulating factors, such as Granulocyte Macrophage Colony Stimulating Factor (GM- CSF, sargramostim), Imiquimod®, mucin-1-mRNA/protamine complex, resimiquimod, and interferon-alpha.

In another embodiment of the composition according to the disclosure, the adjuvant is mucin-1-mRNA/protamine complex, imiquimod, or resimiquimod.

This compositions disclosed herein can be used for parenteral administration, such as subcutaneous, intradermal, intramuscular, intraperitoneal or for oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, $3^{rd}$ Ed. 2000, American Pharmaceutical Association and pharmaceutical press. The composition can be used for a prevention, prophylaxis and/or therapy of adenomateous or cancerous diseases, preferably CRC.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs but if additionally APCs with the respective MHC molecule are added.

In another embodiment the composition according to the present disclosure additionally contains at least one antigen presenting cell.

The antigen-presenting cell (or stimulator cell) typically has an MHC class I or II molecule on its surface and in one embodiment is substantially incapable of itself loading the MHC class I or II molecule with the selected antigen. As is described in more detail below, the MHC class I or II molecule may readily be loaded with the selected antigen in vitro.

In one embodiment, the mammalian cell lacks or has a reduced level or has reduced function of the TAP peptide transporter. Suitable cells which lack the TAP peptide transporter include T2, a human peptide loading deficient cell line that is available from the American Type Culture Collection, 12301 Parklawn Drive, Rockville, Md. 20852, USA under Catalogue No CRL 1992; TAP-deficient cell lines such as T2 can be used as APCs, and due to the lack of TAP nearly all peptides presented by MHC class I will be the peptides under scrutiny used for externally loading the empty MHC class I molecules of these cell lines, hence all effects will clearly attribute to the used peptides.

In another embodiment, the antigen presenting cells are dendritic cells. Suitably, the dendritic cells are autologous dendritic cells which are pulsed with an antigenic peptide. The antigenic peptide may be any suitable antigenic peptide which gives rise to an appropriate T-cell response. T-cell therapy using autologous dendritic cells pulsed with peptides from a tumor associated antigen is disclosed in Murphy et al (1996) The Prostate 29, 371-380, and Tjua et al (1997) The Prostate 32, 272-278.

In another embodiment, the composition containing at least one antigen presenting cell is pulsed or loaded with the peptide.

As an alternative the antigen presenting cell comprises an expression construct encoding the peptide. The polynucleotide may be any suitable polynucleotide. In one embodiment, the polynucleotide is capable of transducing the dendritic cell thus resulting in the presentation of a peptide and induction of immunity.

Conveniently, a nucleic acid of the present disclosure may be comprised in a viral polynucleotide or virus. For example, adenovirus-transduced dendritic cells have been shown to induce antigen-specific anti-tumor immunity in relation to MUC1 (see Gong et al (1997) Gene Ther. 4, 1023-1028). Similarly, adenovirus-based systems may be used (see, for example, Wan et al (1997) Hum. Gene Ther. 8, 1355-1363); retroviral systems may be used (Specht et al (1997) J. Exp. Med. 186, 1213-1221 and Szabolcs et al (1997) Blood particle-mediated transfer to dendritic cells may also be used (Tuting et al (1997) Eur. J. Immunol. 27, 2702-2707); and RNA may also be used (Ashley et al (1997) J. Exp. Med. 186, 1177 1182).

Generally, a composition of the disclosure containing (a) nucleic acid(s) of the disclosure can be administered in a similar manner as those containing peptide(s) of the disclosure, e.g. intravenously, intra-arterially, intra-peritoneally, intramuscularly, intradermally, intratumorally, orally, dermally, nasally, buccally, rectally, by inhalation, or by topical administration.

Due to evasion mechanisms a tumor often develops resistance to the drug it is treated with. The drug resistance may occur during treatment and manifests itself in metastases and recurring tumors. To avoid such a drug resistance a tumor is commonly treated by a combination of drugs and metastases and tumors recurring after a disease free period of time often require a different combination. Therefore, in one aspect of the disclosure the composition is administered in conjunction with a second anticancer agent. The second agent may be administered before after or simultaneously with the composition of the disclosure. A simultaneous administration can e.g. be achieved by mixing the composition of the disclosure with the second anticancer agent if chemical properties are compatible. Another way of a simultaneous administration is the administration of the composition and anticancer agent on the same day independently from the route of administration such that the composition may be e.g. injected while the second anticancer agent is for instance given orally. The composition and second anticancer agent may also be administered within the same treatment course but on different days and/or within separate treatment courses.

In another embodiment, a method for treating or preventing a cancer in a patient is provided, said method comprising administering to the patient a therapeutically effective amount any one of the presently-disclosed compositions.

A therapeutically effective amount will be an amount sufficient to induce an immune response, in particular an activation of a subpopulation of CTLs. A person skilled in the art may easily determine whether an amount is effective by using standard immunological methods, such as those provided in the examples of the present specifications. Another way of monitoring the effect of a certain amount of the composition is to observe the growth of the tumor treated and/or its recurrence.

In another embodiment, the composition is used as an anti-cancer vaccine.

The composition containing peptides or peptide-encoding nucleic acids can also constitute a tumor or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient.

In one aspect, the vaccine is a multiple peptide tumor vaccine for treatment of prostate cancer. In a further aspect, the vaccine comprises a set of tumor-associated peptides selected from SEQ ID NO: 1 to SEQ ID NO: 11 and SEQ ID NO: 13 to SEQ ID NO: 14 which are located and have been identified on primary prostate cells and/or prostate carcinomas. This set includes HLA class I and class II peptides. The peptide set can also contain at least one peptide, such as from influenza core antigen, used as a positive control peptide serving as immune marker to test the efficiency of the intradermal administration. In one particular embodiment, the vaccine consists of 14 individual peptides (according to SEQ ID NO: 1 to SEQ ID NO: 14) with each peptide present in an amount selected from the group consisting of from about 1500 µg to about 75 µg, about 1000 µg to about 175 µg, about 500 µg to about 600 µg, about 578 µg of each peptide, all of which may be purified by HPLC and ion exchange chromatography and appear as a white to off-white powder. The lyophilisate may be dissolved in sodium hydrogen carbonate, and used for intradermal injection within 30 min after reconstitution at room temperature. Total amounts of peptides per 500 µl of solution can vary from about 0.1 to 100 mg, from about 0.1 to 1 mg, and from about 300 µg to 800 µg. Herein, the term "about" shall mean+/−10 percent of the given value, if not stated differently. The person of skill will be able to adjust the actual amount of peptide to be used based on several factors, such as, for example, the immune status of the individual patient and/or the amount of TUMAP that is presented in a particular type of cancer. The peptides might be provided in other suitable forms (sterile solutions, etc.) instead of a lyophilisate.

The compositions may comprise the peptides in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like. By way of example and not limitation, the compositions may comprise the peptides as salts of acetic acid (acetates), ammonium, or hydrochloric acid (chlorides).

In another embodiment, a composition may include sugars, sugar alcohols, amino acids such a glycin, arginine, glutaminic acid and others as framework former. The sugars may be mono-, di- or trisaccharide. These sugars may be used alone, as well as in combination with sugar alcohols. Examples of sugars include glucose, mannose, galactose, fructose or sorbose as monosaccharides, sucrose, lactose, maltose or trehalose as disaccharides and raffinose as a trisaccharid. A sugar alcohol may be, for example, mannitose. In one embodiment, the composition comprises sucrose, lactose, maltose, trehalose, mannit and/or sorbit, In an other embodiment, the composition comprises mannitol.

Furthermore, compositions may include physiological well tolerated excipients (see Handbook of Pharmaceutical Excipients, 5$^{th}$ ed., edited by Raymond Rowe, Paul Sheskey and Sian Owen, Pharmaceutical Press (2006)), such as antioxidants like ascorbic acid or glutathione, preserving agents such as phenole, m-cresole, methyl- or propylparabene, chlorobutanol, thiomersal or benzalkoniumchloride, stabilizer, framework former such as sucrose, lactose, maltose, trehalose, mannitose, mannit and/or sorbit, mannit and/or lactose and solubilizer such as polyethyleneglycols (PEG), i.e. PEG 3000, 3350, 4000 or 6000, or cyclodextrines, i.e. hydroxypropyle-β-cyclodextrine, sulfobutylethyl-β-cyclodextrine or γ cyclodextrine, or dextranes or poloxaomers, i.e. poloxaomer 407, poloxamer 188, or Tween® 20, Tween® 80. In another aspect, one or more well tolerated excipients may be included, selected from the group consisting of antioxidants, framework formers and stabilizers.

In another aspect, the pH for intravenous and intramuscular administration is selected from pH 2 to pH 12, while the pH for subcutaneous administration is selected from pH 2.7 to pH 9.0 as the rate of in vivo dilution is reduced resulting in more potential for irradiation at the injection site. Strickley Robert G., Pharm. Res., 21, NO:2, 201-230 (2004).

In a further aspect, the pharmaceutical preparation comprising peptides, and/or nucleic acid(s) according to the disclosure is administered to a patient that suffers from an adenomateous or cancerous disease that is associated with the respective peptide or antigen. By this, a T cell-mediated immune response can be triggered.

Further disclosed is a composition, wherein the amount of (in particular tumor associated) peptide(s), of nucleic acid(s), or expression vector(s) according to the disclosure as present in the composition is/are tissue, cancer, and/or patient-specific.

In another embodiment, the vaccine is a nucleic acid vaccine. It is known that inoculation with a nucleic acid vaccine, such as a DNA vaccine, encoding a polypeptide leads to a T-cell response. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2 or GM-CSF. The nucleic acid(s) may be substantially pure, or combined with an immune-stimulating adjuvant, or used in combination with immune-stimulatory cytokines, or be administered with a suitable delivery system, for example liposomes. The nucleic acid vaccine may also be administered with an adjuvant such as those described for peptide vaccines above. The nucleic acid vaccine may be administered without adjuvant.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun", may also be used. The peptide or peptide encoded by the nucleic acid may be a fusion protein, for example with an epitope from tetanus toxoid which stimulates CD4-positive T-cells.

Suitably, any nucleic acid administered to the patient is sterile and pyrogen free. Naked DNA may be given intramuscularly or intradermally or subcutaneously. Conveniently, the nucleic acid vaccine may comprise any suitable nucleic acid delivery means. The nucleic acid may also be delivered in a liposome or as part of a viral vector delivery system. In one embodiment, a nucleic acid vaccine, such as a DNA vaccine, is administered into the muscle. In another embodiment, peptide vaccines are administered s.c. or i.d. In a further embodiment, the vaccine is administered into the skin.

It is believed that uptake of the nucleic acid and expression of the encoded polypeptide by professional antigen presenting cells such as dendritic cells may be the mechanism of priming of the immune response; however, dendritic cells may not be transfected but are still important since they may pick up expressed peptide from transfected cells in the tissue ("cross-priming", e.g., Thomas A M, Santarsiero L M, Lutz E R, Armstrong T D, Chen Y C, Huang L Q, Laheru D A, Goggins M, Hruban R H, Jaffee E M. Mesothelin-specific CD8(+) T cell responses provide evidence of in vivo cross-priming by antigen-presenting cells in vaccinated pancreatic cancer patients. J Exp Med. 2004 Aug. 2; 200(3):297-306).

Polynucleotide-mediated immunization therapy of cancer is described in Conry et al (1996) Seminars in Oncology 23, 135-147; Condon et al (1996) Nature Medicine 2, 1122-1127; Gong et al (1997) Nature Medicine 3, 558-561; Zhai et al (1996) J. Immunol. 156, 700-710; Graham et al (1996) Int J. Cancer 65, 664-670; and Burchell et al (1996) 309-313 In: Breast Cancer, Advances in biology and therapeutics, Calvo et al (Eds), John Libbey Eurotext, all of which are incorporated herein by reference in their entireties.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al (1995) Blood 86, 3295-3301; Roth et al (1996) Scand. J. Immunology 43, 646-651). For example, targeting vectors may comprise a tissue- or tumor-specific promoter which directs expression of the antigen at a suitable place.

The vaccine can be dependent from the specific type of cancer that the patient to be treated is suffering from as well as the status of the disease, earlier treatment regimens, the immune status of the patient, and, of course, the HLA-haplotype of the patient. Furthermore, the vaccine can contain individualized components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

In addition to being useful for treating cancer, the peptides disclosed herein are also useful as diagnostics. Since many of the peptides were generated from prostate carcinomas and since it was determined that these peptides are not present in normal tissues, these peptides can be used to diagnose the presence of a cancer.

The presence of the peptides on tissue biopsies can assist a pathologist in diagnosis of cancer. Detection of certain of the disclosed peptides by means of antibodies, mass spectrometry or other methods known in the art can tell the pathologist that the tissue is malignant or inflamed or generally diseased. Presence of groups of presently-disclosed peptides can enable classification or subclassification of diseased tissues.

The detection of the presently disclosed peptides on a diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of the presently-disclosed peptides shows that this mechanism is not exploited by the analyzed cells.

The presently-disclosed peptides might be used to analyze lymphocyte responses against those peptides, such as T cell responses or antibody responses against the peptides or the peptides complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against the presently-disclosed peptides can be considered in the assessment of side effects. Monitoring of lymphocyte responses might also be a valuable tool for follow-up examinations of transplantation therapies, e.g. for the detection of graft versus host and host versus graft diseases.

In yet another aspect thereof, a kit is disclosed comprising (a) a container that contains a composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. In one embodiment, the container is selected from the group consisting of: a bottle, a vial, a syringe, a test tube, or a multi-use container. In another embodiment, the composition is lyophilized.

In one aspect, the kits may comprise a lyophilized formulation of the presently-disclosed compositions and/or vaccines in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. In one embodiment, the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

In one embodiment, upon mixing of the diluent and the lyophilized formulation, the final peptide concentration in the reconstituted formulation is at least 0.15 mg/mL/peptide (=75 µg) and not more than 3 mg/mL/peptide (=1500 µg). The kit may further include other materials desirable from a commercial and user standpoint, including other buffers, diluents, filters, needles, syringes, and package inserts with instructions for use.

The kits may have a single container that contains the formulation of the compositions with or without other components (e.g., other compounds or compositions of these other compounds) or may have distinct container for each component.

Additionally, the kits may include a formulation of the presently disclosed compositions and/or vaccines packaged for use in combination with the co-administration of a second compound (such as adjuvants (e.g. imiquimod), a chemotherapeutic agent, a natural product, a hormone or antagonist, a anti-angiogenesis agent or inhibitor, a apoptosis-inducing agent or a chelator) or a composition thereof. The components of the kit may be pre-complexed or each component may be in a separate distinct container prior to administration to a patient. The components of the kit may be provided in one or more liquid solutions. In one embodiment, the liquid solution is an aqueous solution. In a further embodiment, the liquid solution is a sterile aqueous solution. The components of the kit may also be provided as solids, which may be converted into liquids by addition of suitable solvents, which may be provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. In one embodiment, a therapeutic kit will contain an apparatus (e.g., one or more needles, syringes, eye droppers, pipette, etc.), which enables administration of the agents of the disclosure that are components of the present kit.

The pharmaceutical formulation may be one that is suitable for administration of the peptides by any acceptable route such as oral (enteral), nasal, ophthal, subcutaneous, intradermal, intramuscular, intravenous or transdermal. In one aspect, the administration is subcutaneous and may be administered by an infusion pump.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, secretion of effector molecules, or degranulation. In one embodiment, the T-cell response is the secretion of cytokines induced by the peptide, wherein the peptide is selected from the group consisting of Interferon-gamma, TNF-alpha, or IL-2. In one embodiment, the T-cell response is the secretion of effector molecules induced by peptide, wherein the effector molecule is selected from the group consisting of granzymes and perforins. For MHC class II-restricted T helper cells, effector functions may be peptide induced secretion of cytokines, including but not limited to, IFN-gamma, TNF-alpha, IL-4, IL5, IL-10, or IL-2, or peptide-induced degranulation. Possible effector functions for CTLs and T helper cells are not limited to this list.

Further disclosed are compositions comprising combinations of amino acid sequences of peptides that have the ability to bind to a molecule of the human major histocompatibility complex (MHC) class-I (HLA class I) or II (HLA class II).

The compositions may be used as an effective anti-prostate cancer vaccine that is based on a combination of the peptides.

Another aspect is a method of treating prostate cancer comprising administering to a patient having prostate cancer any of the compositions disclosed herein. These compositions can be administered either with or without accompanying treatment with an immunological adjuvant. If an immunological adjuvant is used, it can be included in the compositions disclosed herein or administered separately via the same route of administration or different routes of administration.

The compositions and methods disclosed herein can be used as a primary therapy, an adjuvant therapy, or a palliative therapy and can be used alone or in conjunction with other therapies, including but not limited to, surgical therapies (including prostatectomy), radiation therapies, and chemotherapies. The disclosed methods further can be used in response to a primary tumour, a biological recurrence, a localized recurrence, or a metastatic recurrence. The presently-disclosed methods can further be used before, in conjunction with, or after androgen deprivation therapy in both androgen-sensitive prostate cancers and androgen-independent prostate cancers.

As used herein, the phrase "androgen-sensitive prostate cancer" shall refer to any prostate cancer in which tumour growth requires androgens.

As used herein, the phrase "androgen-independent prostate cancer" shall refer to any prostate cancer in which tumour growth occurs in the absence of androgens.

As used herein, the phrase "androgen deprivation therapy" refers to any treatment having the primary effect of suppressing androgen signalling or androgen production.

The following examples serve to illustrate certain aspects and are not intended to limit the present disclosure. All references as cited herein are incorporated by reference in their entireties.

EXAMPLES

Example 1

An HLA-binding peptide cocktail was tested in patients with biochemical relapse after radical prostatectomy without diagnostic evidence of metastatic manifestation to determine whether such a composition would be effective at stabilizing and/or increasing PSA doubling times ("DT").

Patient Selection

All patients had a biochemical relapse after initial curative treatment by radical prostatectomy. Biological relapse was defined as an increase of PSA value greater than 50% from the lowest level after surgery or after surgery plus radiation therapy, evaluated by two measurements separated by at least 14 days. Other eligibility criteria included: absence of metastatic disease or local tumor recurrence as determined by bone scan, axial imaging and CT, Eastern Cooperative Oncology Group performance status of 0 or 1, age >45 and <80 years, absence of corticoid or other immunomodulatory therapy; no concomitant radiation, hormonal or chemotherapeutic therapy; no other malignancy, epileptic or pulmonary disease. At the time of being included in the study, all patients were androgen-sensitive and had discontinued androgen deprivation therapy for at least 12 months prior to inclusion. All patients were HLA-A*02 positive. Patient characteristics are shown below at Table 1.

TABLE 1

|  | Total | % | Median | Range |
|---|---|---|---|---|
| Prior neo-/adjuvant treatment | 19 | 100 | | |
| None | 11 | 58 | | |
| Radiation | 3 | 16 | | |
| Intermittent Hormonal Therapy | 2 | 11 | | |
| Rad. + Int. Horm. Therapy | 2 | 11 | | |
| Rad. + Chemotherapy | 1 | 5 | | |
| TNM at RPX | | | | |
| T2a-c R0 | 6 | 32 | | |
| T3a-c R0 | 6 | 32 | | |

TABLE 1-continued

|  | Total | % | Median | Range |
|---|---|---|---|---|
| T2a-c R1 | 3 | 16 | | |
| T3a-c R1 | 3 | 16 | | |
| T3aN2 R0 | 1 | 5 | | |
| Gleason score | | | | |
| 5-7 | 10 | 53 | | |
| 8-10 | 3 | 16 | | |
| Unknown | 6 | 32 | | |
| Age (years) | | | 63 | 55-77 |
| Months between RPX vaccination | | | 41 | 9-124 |
| First relapse post operations in months | | | 14 | 1-90 |
| PSA at vaccination start | | | 0.76 | 0.14-10.80 |

Treatment

In order to prevent tumor escape through genetic mutation and antigen loss, a polyvalent peptide composition targeting a broad spectrum of specific T-cells was used. The composition comprised 13 synthetic HLA-binding peptides specific for both HLA-class I and -class II from prostate-associated antigenic molecules for activation of cytotoxic CD8+ and CD4+ T helper cells. Eleven of the peptides (SEQ ID NO: 1 through SEQ ID NO: 11) comprised HLA-A*0201-restricted epitopes. Two peptides (SEQ ID NO: 13 and SEQ ID NO: 14) comprised HLA class II-binding epitopes. An additional peptide comprising an HLA-A*0201 epitope derived from the influenza virus (SEQ ID NO: 12) was added as a marker peptide for activating recall CD8+ T-cell response. Peptides were emulgated with 500 ml montanide ISA-51 and injected subcutaneously at a dose of 300 mg per individual peptide.

In addition, patients were randomly assigned to receive (1) an immunological adjuvant; (2) hyperthermia; or (3) no immunological adjuvant or hyperthermia. The immunological adjuvants used were (1) imiquimod (Aldara®, Meda Pharma, Bad Homburg, Germany), (2) GM-CSF (Leukine®, Bayer Healthcare, Leverkusen, Germany), and (3) a mucin-1-mRNA/protamine complex as described in Scheel et al., Therapeutic anti-tumor immunity triggered by injections of immunostimulating single-stranded RNA, Eur. J. Immunology 2006; 36(10):2807-2816.

Three patients (Patients 1, 2, and 5) received no immunological adjuvant or hyperthermia.

Four patients (Patients 16, 17, 18, and 19) received mucin-1-mRNA/protamine complex as an immunological adjuvant. In patients receiving mucin-1-mRNA/protamine complex, 110 μg of the immunological adjuvant were emulgated with the peptides and montanide ISA-51. All components were administered in one injection.

Four patients (Patients 3, 7, 8, and 11) received imiquimod as an immunological adjuvant. In these patients, an imiquimod cream was applied topically on the injection site after the peptide treatment and occluded. Patients were instructed to clean the site of imiquimod application with water after 8 hr.

Six patients (patients 4, 6, 9, 12, 14, and 15) received GM-CSF as an immunological adjuvant. In these patients, the immunological adjuvant was injected subcutaneously close to the injection site at a dose of 225 μg.

Two patients (patients 10 and 13) received hyperthermia. In these patients, a heat source maintained at 41° C. was applied to 20 cm$^2$ of exposed abdominal skin at the site of injection directly after the treatment and maintained there for 20 min.

Treatment with the peptide composition, immunological adjuvant, and/or hyperthermia was repeated on Days 7, 14, 28, 42 and 56 following the initial treatment using the same location for each application. Thereafter, if objective regression or stabilization of PSA-value was present, treatment was continued every 4 weeks until Day 420.

Response Evaluation

The treatment response was evaluated by PSA measurement as a surrogate parameter determined at each treatment visit. Hematology and blood chemistry tests were repeated after the first six treatments (at week 8) and every 3 months thereafter. Clinical examinations and digital rectal examinations were performed in an analogous schedule for the evaluation of clinical progression.

Data Analysis

Response was evaluated by calculating geometric mean doubling times. The logarithms of the PSA values for each patient were fitted to straight lines with variable slopes. The switch points between two slopes, the different slopes and the initial value were estimated by the method of least squares using the nonlinear fitting routine. Complete response was defined as a non-measurable PSA value; partial response as a drop of PSA-value of 50%; stable disease as a decrease not larger than 50% or an increase not greater than 10%; and progressive disease as any increase larger than 10% from baseline PSA-value. These measurements had to be confirmed after 4 weeks. The biochemical response of patients who terminated the study was followed until they received further treatment with local radiation or androgen deprivation therapy.

Results

The mean PSA doubling time (DT) prior to treatment was 8.4 months in all patients and increased to 11.2 months at the end of treatment. Four (21%) patients showed a biochemical benefit from the treatment. Clinical tumor recurrence was detected in two patients with progressive PSA values by digital rectal examination and confirmed by PET-CT scan. Treatment response, and therefore PSA-value, differed among patients and could be classified into five different groups of response. The data is compiled at FIG. 2.

PSA Stability and Increase in DT.

Two patients (Patients 3 and 8; 11%) exhibited PSA stability (FIG. 3) during treatment and on follow-up 14 and 16 months after the last application. The average duration of stability from starting treatment was 29.5 months at data cut-off, with an average of 17 treatments (14 and 20) applied. Patient 3 had partial PSA response (>50%) for a period of 9 months, followed by a period of slow PSA rise with a doubling time of 20.5 compared to 9.8 months prior to treatment. Initial PSA relapse prior to the study started 18 months after prostatectomy (pT2pN0 GS 5). Patient 3 had to quit participation because of an allergic reaction at his 20th treatment. Patient 8 exhibited stable disease behavior after the start of treatment. He stopped treatment because of an allergic reaction at the 14th treatment after 10 months. This patient had a pT3b Gleason 3+4 tumor with a PSA nadir of 0.6 ng/ml after radical prostatectomy and showed PSA progression prior study entry after an initial decline postoperatively. His calculated DT increased from 6.6 to 148.0 months. Both patients received dermal imiquimod as an immunological adjuvant (FIG. 4).

Increase in PSA DT Without PSA Stability.

Two patients (Patient 11 and 16, 11%) had an increase in PSA DT during the treatment period, with a concomitant slow increase of PSA-value. The PSA DT of Patient 11 rose from 1.5 to 10.1 months in the first 6 months of treatment. This patient started therapy at a PSA value of 10.8 ng/ml and progressed to 17.8 ng/ml after 6 months of treatment. The study was terminated and hormonal replacement therapy started. In this patient, no visible malignant lesions were seen in a PET-CT scan. Imiquimod was used as an immunological adjuvant. In Patient 16 the DT was 6.1 months at the start of the study. His PSA value decreased and altered the DT into a half-time of 2.7 months in the first 5 months of treatment. Thereafter his statistically calculated DT increased to 14.4 months, which continued for 16 months after the beginning of treatment. At the start of treatment, his PSA-value was 0.29 ng/ml; at the end of follow-up 0.41 ng/ml. He received a mucin-1-mRNA/protamine complex as an immunological adjuvant (FIGS. 3 and 4).

Interim PSA Rise Followed by PSA Decline and Increase in PSA DT.

One patient (Patient 5, 5%) had an uninfluenced PSA increase after the start of treatment and therapy was stopped after the 11th peptide administration at a PSA value of 1.31 ng/ml. Thereafter, his PSA decreased and the DT increased to 20.2 months until the end of follow-up; the patient did not receive any additional treatment during this period. In this patient, no immunological adjuvant was used and peptides were solely emulgated in montanide (FIGS. 3 and 4).

Interim PSA Decline or Stability Followed by Accelerated Rise in PSA.

PSA values of three patients (Patient 7, 15 and 17, 16%) remained stable or declined, which was then followed by an accelerated rise. The DT of Patient 7 was 3.7 months at the start of treatment, and increased to 21.5 months, lasting for 4 months during therapy and progressed thereafter to a DT of 2.8 months. This patient had a pT2b tumor in histology with positive surgical margins. He refused any local radiation therapy (FIG. 3). The DT of Patient 15 was 1.3 months at the start of the study. Prior to the first treatment, the last two consecutive PSA values were determined in our clinic during a 4-month period. This changed the PSA DT results from 1.3 to 25.8 months owing to inter-laboratory differences. During treatment, combined with GM-CSF, the DT diminished to 9.9 months and was stable for 6 months. Then PSA progressed again to a DT of 7.4 months. Interpretation of this PSA course is hampered by the short-term change of the baseline PSA DT prior to starting the treatments. In Patient 17, the PSA DT declined from 10.2 to 4.8 months during treatment after an interim PSA reduction with a half-time of 1.9 within the treatment period, which lasted for 2 months followed by an increase in PSA (FIG. 3).

Progression of PSA

PSA values of 11 patients (58%), progressed unaffectedly with constant PSA DT during the study period and the study was terminated early (FIG. 4). An average of 13 treatments (range 7-18) was applied.

Influence of the Immunological Adjuvant

Out of the eight patients showing a PSA DT increase or PSA value decrease, four received imiquimod as immunological adjuvant. One patient received GM-CSF, two patients the mucin-1-mRNA/protamine complex and one patient had no immunological adjuvant. Out of the two patients treated with local hyperthermia, none had a response or clinical benefit (FIG. 4).

Example 2

Reactivity for specific HLA-class I-binding peptides included in the multi-peptide cocktail was tested following the treatment in Example 1.

In Vitro Amplification of Specific T-Cells

Peripheral blood mononuclear cells from prostate carcinoma patients were obtained at different time-points during vaccination and cryopreserved in 90% fetal calf serum and 10% DMSO in liquid nitrogen. After thawing, approximately $5 \times 10^6$ cells were cultivated (24-well cell culture plate, Greiner Bio-One, Frickenhausen, Germany) in IMDM medium supplemented with 50 U/ml Penicillin, 50 µg/ml Streptomycin (all Biowhittaker, Verviers, Belgium), 10% heat-inactivated human serum (c.c. pro, Neustadt, Germany) and 50 µM beta-mercaptoethanol at 37° C. and 7.5% $CO_2$. Pooled synthetic HLA-class I or HLA-class II binding peptides, respectively were added at day 1, at 1 µg/ml for HLA-class I and at 5 µg/ml for HLA-class II. The culture was supplemented with recombinant human IL-2 (r-hIL2, R&D Systems GmbH, Wiesbaden, Germany) at days 3, 5, 7 and 9 of the T-cell stimulation, promokine, and IL-4 and 7 at day 0 for HLA-class I, and recombinant human IL-2 (r-hIL2, R&D Systems GmbH, Wiesbaden, Germany) at days 3, 5, 7 and 9 of the T-cell stimulation and promokine for HLA-class II.

Enzyme-Linked Immunosorbent Spot (Elispot) Assay

The functionality of expanded T-cells was tested in a standard Interferon-γ ELISPOT assay according to the recommendations of the Immunoguiding program of the Cancer immunotherapy association (CIP). Briefly, cells were harvested at the 12 day of culture, washed, counted and seeded in culture medium on an ELISPOT plate (Millipore, Schwalbach, Germany). Between 0.20 and $0.40 \times 10^6$ cells were tested in duplicates or triplicates, in the presence of i) the peptide-presenting cell line K562-A2 and each individual HLA-class I-binding peptide at 1 µg/ml or ii) each individual HLA-class II-binding peptide at 2.5 µg/ml. PHA (10 µg/ml) or SEB (1 µg/ml) were used as positive control stimuli. Production of IFN-γ was detected with a pair of specific monoclonal antibodies (1D1-k and 7-B6-1, both Mabtech, Nacka Strand, Sweden) after 26 hour incubation at 37° C. and 7.5% $CO_2$. ExtraAvidin-Alkaline Phosphatase and BCIP/NBT substrate (both Sigma-Aldrich) were added for 1 hour and 10 min respectively. ELISPOT analysis was performed using ImmunoSpot readers (Series 3A and 5, Cellular Technology Ltd, Aalen, Germany).

The presence of IFN γ-producing T cells was recorded for each peptide from each patient and tabulated. As can be seen at FIG. 13, eight of the eleven HLA class I peptides induced a response in at least one patient. The most prevalent response was induced by PSMA 711 (SEQ ID NO: 7), which induced peptide reactivity in 25 of the 29 patients analyzed.

Example 3

Reactivity for specific HLA-class II-binding peptides included in the multi-peptide cocktail also was tested following the treatment in Example 1.

Synthetic Peptides and Stimuli

Synthetic peptides used for the stimulation and for functional tests were the HIV-derived epitope (HIV gag 164-181: YVDRFYKTLRAEQASQEV (SEQ ID NO: 15), negative control); PSMA 459-473: NYTLRVDCTPLMYSL (SEQ ID NO: 13) and Survivin 97-111: TLGEFLKLDRERAKN (SEQ ID NO: 14).

In Vitro Amplification of Specific T-Cells

Peripheral blood mononuclear cells from prostate carcinoma patients No. 15 and 26 were obtained at different timepoints during vaccination and cryopreserved in 90% fetal calf serum and 10% DMSO in liquid nitrogen. After thawing, approximately 5×10⁶ cells were cultivated (24-well cell culture plate, Greiner Bio-One, Frickenhausen, Germany) in IMDM medium supplemented with 50 U/ml Penicillin, 50 µg/ml Streptomycin (all Biowhittaker, Verviers, Belgium), 10% heat-inactivated human serum (c.c. pro, Neustadt, Germany) and 50 µM beta-mercaptoethanol at 37° C. and 7.5% $CO_2$. Pooled synthetic HLA-class II binding peptides were added at day 1, each at 5 µg/ml and the culture was supplemented with recombinant human IL-2 (r-hIL2, R&D Systems GmbH, Wiesbaden, Germany) at days 3, 5, 7 and 9 of the T-cell stimulation. After a 12 day stimulation period, cells were harvested, washed, counted and restimulated with peptides (10 µg/ml) for 6 hours. IFN-γ-secreting cells were labelled with IFN-γ Catch Reagent and IFN-γ PE Antibody according to the MACS IFN-γ Secretion Assay protocol (Miltenyi Biotech, Bergisch Gladbach, Germany), then sorted in 96 well plates containing IMDM 10% HS with 150 U/ml IL-2, 1 µg/ml PHA and irradiated allogenic feeders (PBMC+LG2-EBV) using a FACSAria (BD Biosciences). IL-2 (150 U/ml) was added every 4 days and feeder cells every three weeks.

Intracellular Cytokine Staining

Effectors were harvested, washed and stimulated in a standard assay with the HIV, PSMA, and Survivin peptides at 5 µg/ml or PMA and Ionomycin (50 ng/ml and 1 µM, respectively) in the presence of Golgi-STOP (BD Biosciences, Heidelberg, Germany) and Brefeldin A (10 µg/ml, Sigma-Aldrich) following the manufacturers instructions. Following an incubation period of 4-6 hours, cells were washed in PBS 2% FCS 0.02% $NaN_3$ and stained with monoclonal antibodies (MoAb) CD4-APC-Cy7 (BD Biosciences) and CD8-PE-Cy7 (Beckman Coulter) for 20 min at 4° C. in the dark. After a washing step, cells were permeabilized 20 min with Cytofix/Cytoperm reagent (BD Biosciences) then stained for intracellular IFN-γ using a monoclonal IFN-γ-FITC antibody (BD Biosciences). Cell acquisition was performed on a Cytometer Canto II using the software Diva and analysis with FlowJo (BD Biosciences). In multifunctional tests, CD4-APC-Cy7 and CD8-PerCP were used for cell membrane staining and IFN-g PE-Cy7, TNF-Pacific Blue, IL-2-PE for intracellular staining (all BD Biosciences, except TNF-Pacific Blue, Biolegend). CD107a-FITC (BD Bioscience) was added during the stimulation period at 1.5 µl/test.

Tests of T-Cell Clone Functionality Using Autologous Dendritic Cells

Monocyte-derived, immature autologous DCs were generated by cultivating monocytes for seven days in IMDM 10% HS, 1% PenStrep, 50 µM β-Mercaptoethanol supplemented with 1000 U/ml IL-4 and 800 U/ml GM-CSF. For functional experiments, DC were either loaded with the relevant HLA-class II binding peptides (HIC, Survivin or PSMA, 10 µg/ml) or pulsed with recombinant proteins (Survivin, PSMA or RAP-80, 20 µg/ml), harvested, washed several times and incubated with specific CD4+ T cell clones at a DC:effector ratio of 1:5 for 12 hours before intracellular cytokine staining.

For control experiments, 1 µg recombinant proteins were pretreated in 100 µl PBS, pH 7.2, with 10 µg proteinase K (Macherey-Nagel, Düren, Germany) in the presence of 1 mM $CaCl_2$ for 2 h at 37° C. Alternatively, DCs were fixed in 0.05% final glutaraldehyde (Sigma) for 15 s. Reaction was stopped with 0.2 M L-lysine (Sigma) and DC washed twice before loading with peptides or proteins.

Determination of HLA-class II restriction. Peptide presentation assays were performed using 12-day peptide-presensitized PBMC of patients n° 15 and 26 as effector cells and peptide-loaded (10 µg/ml peptide, overnight in IMDM 2% FCS) EBV-transformed cell lines as stimulators (see HLA-DR, DP and DQ alleles in FIG. 21) at a ratio of 1 effector for 1 peptide-presenting cell. After 5 hrs co-incubation, intracellular cytokine staining was done as previously described.

The invention claimed is:

1. A composition comprising at least two HLA-binding peptides, wherein:
   (a) at least one of the at least two HLA-binding peptides is a peptide consisting of an epitope selected from the group consisting of: SEQ ID NO: 17 and SEQ ID NO: 23, and optionally 1 to 12 additional amino acids distributed in any ratio on the N terminus and C-terminus of the epitope; and
   (b) at least one of the at least two peptides is a peptide consisting of an epitope selected from the group consisting of: SEQ ID NO: 7 and SEQ ID NO: 1, and optionally 1 to 12 additional amino acids distributed in any ratio on the N-terminus and C-terminus of the epitope.

2. The composition of claim 1, comprising:
   (a) an HLA-binding peptide consisting of SEQ ID NO: 1 and optionally 1 to 12 additional amino acids distributed in any ratio on the N-terminus and C-terminus of the epitope; and
   (b) an HLA-binding peptide consisting of SEQ ID NO: 7, and optionally 1 to 12 additional amino acids distributed in any ratio on the N-terminus and C-terminus of the epitope; and (c) an HLA-binding peptide consisting of SEQ ID NO: 17, and optionally 1 to 12 additional amino acids distributed in any ratio on the N-terminus and C-terminus of the epitope; and
   (d) an HLA-binding peptide consisting of SEQ ID NO: 23, and optionally 1 to 12 additional amino acids distributed in any ratio on the N-terminus and C-terminus of the epitope.

3. The composition of claim 1, wherein said composition comprises at least three HLA binding peptides, wherein at least two of the HLA binding peptides consist of an amino acid sequence selected from the group consisting of SEQ ID NO: 7 and SEQ ID NO: 1.

4. The composition of claim 1, wherein said composition comprises at least three HLA binding peptides, wherein at least two of the HLA binding peptides consist of an amino acid sequence selected from the group consisting of SEQ ID NO: 1 and SEQ ID NO: 7; and at least one of the HLA binding peptides consists of an amino acid sequence selected from the group consisting of SEQ ID NO: 17 and SEQ ID NO: 23.

5. The composition of claim 1, wherein said composition comprises at least three HLA binding peptides, wherein at least two of the HLA binding peptides consist of an amino acid sequence selected from the group consisting of SEQ ID NO: 1 and SEQ ID NO: 7 and at least one of the HLA binding peptides is selected from the group consisting of SEQ ID NO: 17 and SEQ ID NO: 23, wherein at least one peptide is selected according to an HLA set of a subject to be treated.

6. The composition of claim 1, wherein said composition comprises at least four HLA binding peptides consisting of an amino acid sequence selected from the group consisting of SEQ ID NO: 1, SEQ ID NO: 7, SEQ ID NO: 17, and SEQ ID NO: 23.

7. The composition of claim 6, wherein at least one of the peptides is a class II peptide.

8. The composition of claim 1, wherein said composition comprises SEQ ID NO: 1, and SEQ ID NO: 7.

9. The composition of claim 1, wherein the composition comprises peptides consisting of amino acid sequences according to SEQ ID NO: 1 and SEQ ID NO: 7, and optionally at least one peptide selected from the group consisting of SEQ ID NO: 17 and SEQ ID NO: 23.

10. The composition of claim 1, further comprising an immunological adjuvant.

11. The composition of claim 10, wherein said immunological adjuvant comprises a Toll-like receptor agonist.

12. The composition of claim 11 wherein said Toll-like receptor agonist is a Toll-like receptor-7 agonist.

13. The composition of claim 10 comprising an immunological adjuvant selected from the group consisting of GMCSF and Imiquimod.

14. The composition of claim 10 comprising a mixture of immunological adjuvants.

15. The composition of claim 14 comprising a mixture of two or three immunological adjuvants.

16. A method for treating prostate cancer, comprising administering to a patient an effective amount of the composition according to claim 1.

17. The method of claim 16, wherein said prostate cancer is androgen sensitive and the patient has not received androgen deprivation therapy.

18. The method of claim 16, wherein said prostate cancer is androgen-insensitive.

19. The composition of claim 1 wherein said HLA-binding peptides are in the form of a pharmaceutically acceptable salt.

20. The composition of claim 1 which is in lyophilized form.

* * * * *